(12) United States Patent
Wittorff

(10) Patent No.: US 11,090,263 B2
(45) Date of Patent: *Aug. 17, 2021

(54) TABLETED CHEWING GUM SUITABLE FOR ACTIVE PHARMACEUTICAL INGREDIENTS

(71) Applicant: FERTIN PHARMA A/S, Vejle (DK)

(72) Inventor: Helle Wittorff, Vejle Øst (DK)

(73) Assignee: FERTIN PHARMA A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,362

(22) Filed: May 22, 2018

(65) Prior Publication Data

US 2019/0358159 A1    Nov. 28, 2019

(51) Int. Cl.
*A61K 9/68*    (2006.01)
*A61K 9/20*    (2006.01)

(52) U.S. Cl.
CPC .......... *A61K 9/0058* (2013.01); *A61K 9/2018* (2013.01); *A61K 9/2027* (2013.01); *A61K 9/2086* (2013.01); *A61K 9/2095* (2013.01)

(58) Field of Classification Search
None
See application file for complete search history.

(56) References Cited

U.S. PATENT DOCUMENTS

| | | | |
|---|---|---|---|
| 4,627,977 A | 12/1986 | Gaffar et al. | |
| 4,820,506 A | 4/1989 | Kleinberg et al. | |
| 5,576,014 A | 11/1996 | Mizumoto et al. | |
| 5,874,068 A | 2/1999 | Engelman et al. | |
| 6,024,981 A | 2/2000 | Khankari et al. | |
| 6,146,661 A | 11/2000 | Hoshino | |
| 7,067,149 B1 | 6/2006 | Chauveau et al. | |
| 8,435,542 B2 | 5/2013 | Manley et al. | |
| 8,658,139 B1 | 2/2014 | Cutler | |
| 2003/0022912 A1 | 1/2003 | Martino et al. | |
| 2003/0215502 A1 | 11/2003 | Pruss et al. | |
| 2009/0311320 A1* | 12/2009 | Oury | A61K 45/06 424/465 |
| 2011/0123462 A1 | 5/2011 | Mordas et al. | |
| 2011/0250247 A1 | 10/2011 | Boghmans et al. | |
| 2013/0302387 A1 | 11/2013 | Pedersen | |
| 2014/0328973 A1* | 11/2014 | Nielsen | A23G 4/06 426/2 |
| 2015/0101627 A1* | 4/2015 | Marshall | A24B 13/00 131/352 |
| 2016/0120793 A1 | 5/2016 | Abdalla et al. | |
| 2016/0145203 A1 | 5/2016 | Gambogi et al. | |
| 2018/0140521 A1 | 5/2018 | Geonnotti et al. | |
| 2018/0140554 A1 | 5/2018 | Wittorff | |
| 2018/0140591 A1 | 5/2018 | Wittorff et al. | |

FOREIGN PATENT DOCUMENTS

| | | |
|---|---|---|
| CN | 1709229 A | 12/2005 |
| EP | 0413427 A1 | 2/1991 |
| EP | 0497439 A1 | 2/1991 |
| EP | 0913148 A1 | 6/1999 |
| EP | 0922464 A1 | 6/1999 |
| EP | 1369109 A1 | 10/2003 |
| GB | 1526020 | 9/1978 |
| WO | 9932092 A1 | 7/1999 |
| WO | 02102357 A1 | 12/2002 |
| WO | 2004068964 A1 | 8/2004 |
| WO | 2006063189 A2 | 6/2006 |
| WO | 2009007768 A1 | 1/2009 |
| WO | 2009016133 A1 | 2/2009 |
| WO | 2009080023 A1 | 7/2009 |
| WO | 2010104563 A2 | 9/2010 |
| WO | 2012085043 A2 | 6/2012 |
| WO | 2013125350 A1 | 8/2013 |
| WO | 2016061486 A1 | 4/2016 |
| WO | 2018091048 A1 | 5/2018 |
| WO | 2018091050 A1 | 5/2018 |
| WO | 2018093501 A1 | 5/2018 |

OTHER PUBLICATIONS

Roquette (Signet Chemical Corp., Products, SWEETPEARL, available at http://www.signetchem.com/product.aspx?prdid=1044, accessed on May 13, 2019).*
Aslani, A., et al., Medicated chewing gum, a novel drug delivery system, J Res Med Sci. Apr. 2015; 20(4): 403-411.*
Patent Cooperation Treaty: PCT Application No. PCT/DK2016/050377: International Search Report and Written Opinion; 10 pages; dated Aug. 3, 2017; Ceyte, Mathilde.
Patent Cooperation Treaty: PCT Application No. PCT/DK2017/050342: International Search Report and Written Opinion; 13 pages; dated Nov. 30, 2017; Ceyte, Mathilde.
Patent Cooperation Treaty: PCT Application No. PCT/DK2017/056554: International Search Report and Written Opinion; 10 pages; dated Nov. 30, 2017; Ceyte, Mathilde.
Module. (1992) In C.G.Morris (Ed.), Academic Press Dictionary of Science and Technology. (4th ed.) [Online] Oxford: Elsevier Science & Technology. Available at http://search.credoreference.com/content/entry/apdst/module/0.
Patent Cooperation Treaty: International Search Report and Written Opinion of PCT/DK2019/050152; Gimenez Miralles, J.; dated Aug. 22, 2019; 11 pages.
Patent Cooperation Treaty: International Search Report and Written Opinion of PCT/DK2019/050157; Nyeki, Agnes; dated Sep. 16, 2019; 11 pages.
Patent Cooperation Treaty: International Search Report and Written Opinion of PCT/DK2019/050154; Gimenez Miralles, J.; dated Aug. 22, 2019; 11 pages.
Patent Cooperation Treaty: International Search Report and Written Opinion of PCT/DK2019/050155; Nyeki, Agnes; dated Sep. 20, 2019; 12 pages.
Patent Cooperation Treaty: International Search Report and Written Opinion of PCT/DK2019/050156; Hartinger, Stefan; dated Sep. 20, 2019; 17 pages.
Patent Cooperation Treaty: International Search Report and Written Opinion of PCT/DK2019/050160; Hartinger, Stefan; dated Sep. 20, 2019; 17 pages.

(Continued)

*Primary Examiner* — H. Sarah Park

(57) ABSTRACT

The invention relates to a tableted chewing gum suitable for active pharmaceutical ingredients, the chewing gum comprising a population of particles, the population of particles comprising a) directly compressible (DC) sugar alcohol particles, b) non-directly compressible (non-DC) sugar alcohol particles and c) particles comprising gum base, the gum base comprising at least 5% by weight of elastomer.

20 Claims, 2 Drawing Sheets

(56) References Cited

OTHER PUBLICATIONS

Patent Cooperation Treaty: International Search Report and Written Opinion of PCT/DK2019/050153; Hartinger, Stefan; dated Sep. 30, 2019; 18 pages.

Stefan W. Wessel et al.: "Potential benefits of chewing gum for the delivery of oral therapeutics and its possible role in oral healthcare", Expert Opinion on Drug Delivery, vol. 13, No. 10, Jun. 3, 2016 (Jun. 3, 2016), pp. 1421-1431, XP055609672, GB ISSN: 1742-5247, DOI: 10.1080/17425247.2016.1193154 p. 1422; table 1.

Bolhuis GK Rexwinkel EG Zuurman K: "Polyols as filler-binders for disintegrating tablets prepared by direct compaction", Drug Development and Industrial Pharmacy, New York, NY, US, vol. 35, No. 6, Jun. 2009 (Jun. 2009), pp. 671-677, XP008162413, ISSN: 0363-9045, DOI: 10.1080/03639040802587799 the whole document.

Patent Cooperation Treaty: International Search Report and Written Opinion of PCT/DK2019/050154; Nyeki, Agnes; dated Sep. 20, 2019; 12 pages.

Patent Cooperation Treaty: International Search Report and Written Opinion of PCT/DK2019/050159; Gimenez Miralles, J; dated Aug. 22, 2019; 11 pages.

\* cited by examiner

TABLETED CHEWING GUM SUITABLE FOR ACTIVE PHARMACEUTICAL INGREDIENTS

TECHNICAL FIELD

The invention relates to a tableted chewing gum suitable for active pharmaceutical ingredients.

BACKGROUND

Oral tablets for delivery of active pharmaceutical ingredients are well-known in the art. A challenge in relation to such tablets is that many of such tablets are less than attractive to the user of the tablet. This challenge is significant as users are more and more focused on taste or oral displeasure and it affects the effectiveness and the options available for such oral tablets. This challenge is in particular relevant in relation to oral tablets designed for delivery of active pharmaceuticals and in particular in relation to tablets including compounds for delaying or modifying the release of active pharmaceutical ingredients as displeasure may then be prolonged.

SUMMARY

The invention relates to a tableted chewing gum suitable for active pharmaceutical ingredients, the chewing gum comprising a population of particles, the population of particles comprising a) directly compressible (DC) sugar alcohol particles, b) non-directly compressible (non-DC) sugar alcohol particles and c) particles comprising gum base, the gum base comprising at least 5% by weight of elastomer.

The tableted chewing gum according to the present invention features an attractive mouthfeel where the combination of gum base, in particular a certain amount of elastomer present in the gum base, provides a combined impressive taste and chew impression, which is different from conventional DC sugar alcohols.

Particularly, an advantage of the present invention may be that a very pleasant mouthfeel is obtained by a synergy between the non-DC sugar alcohols, which may promote induced saliva generation, and the gum base comprising at least 5% by weight of elastomers also promoting saliva generation due to the resistance felt by a user during chewing. This combined effective saliva generation also promotes disintegration of a part of the chewing, which again promotes contacting the oral mucosa with the non-DC sugar alcohols from the partly disintegrated chewing gum, thereby also further facilitating saliva generation. Thus, the non-DC sugar alcohols and the particles comprising gum base both have a direct contribution to saliva generation as well as an indirect contribution due to the disintegration a part of the chewing gum. In some embodiments, where e.g. non-DC sugar alcohols and particles comprising gum base are separated into different modules, the gum base free module may disintegrate more or less completely or be chewed into the gum base.

Besides several other advantageous the inventive chewing gum exhibits an impressing initial chew feel due to the fact that saliva generation is promoted by the applied non-DC sugar alcohol.

The specific use of a relatively high proportion of elastomer in the gum base may effectively be used for modification of the release of active ingredients in terms of time and amount and the elastomer may also provide robust structure of the tablet facilitating that it is chewed into a coherent residual containing water-insoluble components. Some active ingredient may risk invoking disintegration of the residual whereas an elastomer may increase the coherence and compensate for the aggressive active ingredients.

It is thus noted that the initial cohering of the particles comprising gum base are improved through the use of the non-DC sugar alcohol, but also that several other advantages with respect to texture, taste and mouthfeel may be easily obtained within the scope of the invention. Such effects include taste masking, flavor burst, improvement of sweetness, etc.

Other advantageous applications within the scope of the invention includes the user of the chewing gum for active ingredients, such as active pharmaceutical ingredients, and oral care, such as dental care. The chewing gum is thus a very attractive carrier of typical ingredients relevant for oral care, such as anti-plaque agent, whiteners, anti-bacterial agents, etc. It is here noted that the improved salivation effect of the chewing gum is the perfect match in relation to an chewing gum which may as such be used as a carrier of relevant active ingredients, but the coherent residue may from the start of mastication and subsequently serve as an abrasive even after most of the oral care ingredients has been released.

Another advantageous application within the scope of the invention is related to nutraceuticals. Several nutraceuticals may easily be carried and released from the inventive oral tablet, but the increased salivation effect may also serve as advantageous promoter of release from both the tablet matrix but also from nutraceutical mixed with the coherent residue during the initial chewing.

In an embodiment of the invention, the non-DC sugar alcohol particles have not been granulated prior to tableting.

Thus, the non-DC sugar alcohol particles are provided as non-granulated particles.

Another more physical understandings, not conflicting with the above definition in relation to some relevant sugar alcohols, such as erythritol, xylitol, maltitol, lactitol and other sugar alcohols being non-DC in its pure form.

These are typically available in a non-DC form of the relevant sugar alcohol as particles which have not been preprocessed by granulation with other sugar alcohols or binders for the purpose of obtaining so-called direct compressible particles (DC) on the basis of sugar alcohol particles which are by themselves not suitable for direct compression. Such non-DC particles of sugar alcohol may typically consist of the sugar alcohol or at least comprise very high quantities of the sugar alcohol. Therefore, non-DC sugar alcohol particles may be particles consisting of sugar alcohol, which is non-directly compressible in its pure form. Examples of sugar alcohols which are non-directly compressible when provided as particles consisting of the sugar alcohol in question include erythritol, xylitol, maltitol, mannitol, lactitol, isomalt, etc.

As a supplementing explanation, many of the most relevant sugar alcohols in relation to the present invention is those sugar alcohols which are available in specially adapted DC-grades obtained through granulation with another compound, typically a binder.

Therefore, preferred non-DC grades of sugar alcohol may include pure sugar alcohol particles.

In an embodiment of the invention, the active ingredient is a nutraceutical.

In the present context, the term "nutraceutical" refers to a pharmaceutical-grade and standardized nutrient.

In an embodiment of the invention, the chewing gum comprises flavor in an amount of 1-10% by weight of the chewing gum.

According to an embodiment of the invention, the chewing gum comprises flavor in an amount of 1-6% by weight of the chewing gum, such as 2-6% by weight of the chewing gum.

In embodiments of the present invention, the chewing gum comprises one or more flavoring agents selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In an embodiment of the invention the flavor is a powder flavor.

In an embodiment of the invention the chewing gum comprises a first module comprising at least a part of the population of particles, the first module comprising at least a portion of the flavor.

In an embodiment of the invention the chewing gum comprises a second module comprising at least a part of the population of particles or a second population of particles, the second module comprising at least a portion of the flavor.

In an embodiment of the invention, the chewing gum is designed to release at least 50% by weight of the flavor within 20 seconds from onset of mastication.

The above release of flavor applies at a chew rate of one chew per second.

In an embodiment of the invention, the chewing gum is designed to be masticated into a coherent residual containing water-insoluble components.

In an embodiment of the invention, the gum base comprises at least 10% by weight of elastomer.

In an embodiment of the invention, the elastomer is selected from styrene-butadiene rubber (SBR), butyl rubber, polyisobutylene (PIB), and combinations thereof and the gum base comprises at least 15% by weight of elastomer.

In an embodiment of the invention, the elastomer is selected from styrene-butadiene rubber (SBR), butyl rubber, polyisobutylene (PIB), and combinations thereof and the gum base comprises between 15% and 25% by weight of elastomer.

In an embodiment of the invention the gum base comprises at least 15% by weight of elastomer.

In an embodiment of the invention the gum base comprises between 15% and 25% by weight of elastomer.

In an embodiment of the invention the gum base comprises between 17% and 23% by weight of elastomer.

In an embodiment of the invention, the chewing gum comprises at least 1% by weight of elastomer.

In an embodiment of the invention, the elastomer is selected from styrene-butadiene rubber (SBR), butyl rubber, polyisobutylene (PIB), and combinations thereof.

The applied elastomer may within the scope of the invention also include polyvinyl acetate (PVA). It is well-known within the art that PVA may be applied both as an elastomer or as a resin. The application of PVA typically depends on the molecular weight of the PVA. Within the present invention, a PVA may be applied as an elastomer when having an average molecular weight of higher than an average molecular weight (Mw) of 50000 g/mol or higher.

Conversely, within the present invention, PVA may be applied as a resin when having an average molecular weight (Mw) below 50000 g/mol.

In an embodiment of the invention, the chewing gum comprises a first module and a second module. The first module may e.g. comprise a) DC sugar alcohol particles and b) non-DC sugar alcohol particles. The second module may comprise c) particles comprising gum base.

In an advantageous embodiment of the invention said population of particles is tableted into a first module and combined with a second population of particles that is tableted into a second module.

In an advantageous embodiment of the invention a) and b) is comprised in a first module and c) is comprised in a second module.

Thus, the chewing gum comprises a first module and a second module, the first module comprising a) DC sugar alcohol particles and b) non-DC sugar alcohol particles, the second module comprising c) particles comprising gum base.

In an advantageous embodiment of the invention a) and b) is tableted into a first module and c) is tableted into a second module, wherein the first module is free of gum base.

Thus, a) DC sugar alcohol particles and b) non-DC sugar alcohol particles are tableted into a first, gum base free module whereas and c) particles comprising gum base are tableted into a second module. The second module may or may not comprise DC sugar alcohol particles and/or non-DC sugar alcohol particles.

In an advantageous embodiment of the invention a) and b) is tableted into a first module and c) is tableted into a second module.

In an embodiment of the invention, the particles comprising gum base have an average particle size of at least 400 µm, such as between 400 µm and 1400 µm.

According to an embodiment of the invention, the particles comprising gum base consists of gum base. When the particles comprising gum base consists of gum base, they typically have an average particle size between 800 µm and 1400 µm.

In an embodiment of the invention, the chewing gum comprises at least 20% by weight of gum base.

In an embodiment of the invention the chewing gum comprises at least 30% by weight of gum base.

In an embodiment of the invention the chewing gum comprises between 20% and 60% by weight of gum base.

In an embodiment of the invention, the gum base comprises at least 5% by weight of resins.

According to an advantageous embodiment of the invention, the gum base comprises at least 10% by weight of resins, such as at least 15% by weight of resins, such as at least 20% by weight of resins.

According to a further advantageous embodiment of the invention, the gum base comprises at least 30% by weight of resins, such as at least 40% by weight of resins, such as at least 45% by weight of resins.

In an advantageous embodiment the content of resin is from 40-60% by weight of the gum base.

In an embodiment of the invention, the, the gum resins are selected from the natural resins and/or synthetic resins including low molecular weight polyvinyl acetate (PVA).

In an embodiment of the invention, the particles comprising gum base comprises gum base in an amount of 20-99.9% by weight.

In an embodiment of the invention, the particles comprising gum base consists of gum base.

In an embodiment of the invention, the chewing gum comprises
- elastomer in the range of 1-15% by weight of the chewing gum,
- natural and/or synthetic resin in the range of 5-35% by weight of the chewing gum,
- water insoluble components different from the elastomer and resin in the range of 5-30% by weight of the chewing gum, and
- water soluble components, such as sugar alcohols, in the range of 50-89% by weight of the chewing gum.

Water insoluble components different from the elastomer and resin in the range of 5-30% by weight of the chewing gum e.g. includes softeners and fillers.

In an embodiment of the invention the chewing gum comprises water soluble components, such as sugar alcohols, in the range of 30-89% by weight of the chewing gum.

In an embodiment of the invention, a) and b) is comprised in a first module and c) is comprised in a second module, wherein c) the particles comprising gum base comprises
- elastomer in the range of 1-15% by weight of the chewing gum,
- natural and/or synthetic resin in the range of 5-35% by weight of the chewing gum,
- water insoluble components different from the elastomer and resin in the range of 5-30% by weight of the chewing gum, and
- water soluble components, such as sugar alcohols, in the range of 20-89% by weight of the chewing gum.

Water insoluble components different from the elastomer and resin in the range of 5-30% by weight of the chewing gum e.g. includes softeners and fillers.

In a further embodiment, a) and b) is comprised in a first module and c) is comprised in a second module, wherein c) the particles comprising gum base comprises, wherein the second module comprise water soluble components, such as sugar alcohols, in the range of 50-89% by weight of the chewing gum.

Thus, a synergy between utilization of non-DC sugar alcohol particles as a disintegration promoter due to the lower mechanical strength and also as a salivation promoter in combination with a second module, which can provide additional mechanical strength, thereby acting as a carrier module. This is especially advantageous when the second module contributes to an attractive mouthfeel by a high content of DC sugar alcohols and particles comprising gum base, which also provides mechanical strength to the chewing gum. The advantageous disintegration thus of course refers to a module containing no gum base, but it may also refer to a module having a population of particles comprising gum base, as these gum base-containing particles may initially be kept in a sugar alcohol matrix which needs to be disintegrated and dissolved very fast during the initial mastication One advantage of the above embodiment may be that the second module may have a higher mechanical strength, e.g. by means of a different composition comprising e.g. a very large amount of direct compressible ingredients, such as DC sugar alcohols and particles comprising gum base.

A further advantage of the above embodiment may be that the second module may have a higher loading capacity for e.g. active ingredients, partly due to the higher obtainable mechanical strength achievable by large amounts of direct compressible ingredients, such as DC sugar alcohols and particles comprising gum base.

Thus, in an embodiment a) and b) is comprised in a first module and c) is comprised in a second module, and c) the particles comprising gum base comprises. The first module may be tableted before the second module, or vice versa. The particles comprising gum base are included in the second module. Alternatively, the particles comprising gum base may be included in the first module or in both the first and second modules. In some embodiments, the chewing gum may comprise one or more further modules. When the gum base is present in one module, the gum base containing module is preferable tableted first. The further module may also comprise particles comprising gum base, or be free of gum base.

In an embodiment of the invention the oral chewing gum comprises at least two modules. A module in the context of the invention is referring to a group of particles which has been compressed into a volume which is comparable to the size of the chewing gum in the sense that it is not insignificant compared to the chewing gum. A chewing gum comprising two or more modules will thus have module sizes which each are comparable to the volume of the complete chewing gum. Comparable in the present context means that the modules are not understood as small particles and a module should at least be greater than $1/20$ of the complete chewing gum volume, preferably greater than $1/10$ of the complete chewing gum volume.

The module may typically be gathered from a plurality of compressed particles and have a weight which is greater than 0.2 gram and less than 10 grams.

In an embodiment of the invention a module is defined as a plurality of particles being compressed together to form a gathered module of particles.

In an embodiment of the invention the chewing gum a plurality of chewing gum modules. In the present context the application of e.g. two modules are in particular advantageous as the use of non-DC sugar alcohols by nature may result in a more fragile chewing gum or at least the module in which the non-DC sugar alcohols are. In other words, non-DC sugar alcohols may be present primarily in one module thereby optimizing the desired salivation and sensory experience from the module and the chewing gum as such whereas another module may serve as a support ensuring that the desired stability and friability of the complete chewing gum is obtained.

According to an embodiment of the invention, the chewing gum has two modules. Optionally, a coating may be applied around the two modules to form the final chewing gum.

An advantage of using two modules is described above, but it should also be noted that this effect may also be obtained when applying layers of very different nature. Such application may e.g. include the use of a gum module and a non-gum module, where the non-gum module is containing the non-DC sugar alcohol particles. In this way, the non-gum layer may release the advantageous non-DC sugar alcohols and the gum layer may both stabilize the chewing gum as described above but also interact with the non-DC sugar alcohols during in particular the initial release for establishment of a very pleasant and impressing initial chew phase. This includes and increased saliva and moisture experience.

In an embodiment of the invention the chewing gum comprises a first module having a first composition and a second module having a second composition, where the first composition is different from the second composition.

In an embodiment of the invention a) and b) is comprised in a first module and c) is comprised in a second module, where the second module is free of non-DC sugar alcohols.

In one embodiment, the second module comprises a large amount of DC sugar alcohols, such as larger amounts than the first module. For example, the second module may comprise at least 30% by weight of DC sugar alcohols, such as at least 50% by weight of DC sugar alcohols, such as at least 70% by weight of sugar alcohols. In an example embodiment, the second module may comprise between 50 and 99.9% by weight of sugar alcohols, such as between 70 and 99% by weight of sugar alcohols.

The amount of DC sugar alcohol may depend on the type and amount of active ingredient applied in the chewing gum, as well as the amount of gum base used in the chewing gum.

In an embodiment of the invention the second module is tableted before the first module.

In an embodiment of the invention, the non-DC particles providing the chewing gum with a plurality of discrete non-DC areas, where the non-DC areas are evenly distributed in the chewing gum or at least one module of the chewing gum.

One advantage of the above embodiment may be that the even distribution of the non-DC areas promotes an effective disintegration of the module upon mastication, e.g. due to lower mechanical strength contribution from the non-DC sugar alcohol particles, thereby facilitating effective contacting of the resulting mastication fragments formed by the mastication with saliva, again increasing dissolving a module or part of the chewing gum. Also, the even distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the even distribution to facilitate effect dispersion of mastication fragments in the oral cavity upon mastication.

In an embodiment of the invention, the non-DC particles provide the chewing gum with a plurality of discrete non-DC areas, where the non-DC areas are evenly distributed in a gum base free module of the chewing gum.

In an embodiment of the invention, the non-DC particles provide the chewing gum with a plurality of discrete non-DC areas.

In an embodiment of the invention, a series of at least 10 of said chewing gums each comprising a gum base free module, the gum base free module comprising said non-DC sugar alcohol particles in an amount varying with a relative standard deviation (RSD) below 10%.

One advantage of the above embodiment may be that uniform product may be obtained having low variation in the amount of non-DC sugar alcohol between gum base free modules of chewing gums. Consequently, the functionality provided by non-DC areas in the gum base free modules of the chewing gum may provide low variation between chewing gums.

It is noted that the reference to RSD and a sequence of chewing gums typically refers to a chewing gum series of a production line.

Furthermore, the RSD of the non-DC sugar alcohol between gum base free modules of chewing gums is a measure of the degree of even distribution of the non-DC areas provided by the non-DC sugar alcohol particles. Therefore, having an RSD below 10% in a series of at least 10 chewing gums indicates an even distribution of the non-DC areas. Having evenly distributed non-DC areas facilitates a high salivation since the non-DC areas are effectively distributed in the mouth upon mastication and a resulting disintegration of the chewing gum.

In an embodiment of the invention, a series of at least 10 of said chewing gums comprises a gum base free module comprising said non-DC sugar alcohol particles in an amount varying with a relative standard deviation (RSD) below 5%.

An advantageous method of dosing non-DC sugar alcohols into a composition for a large number of tablets has been established, which facilitates an exact dosing of the non-DC sugar alcohols in a series of chewing gums. This means that large-scale production of chewing gums comprising non-DC sugar alcohols is made possible with improved results concerning distribution of the non-DC areas in the chewing gums and thereby an improved RSD between the gum base free modules of the chewing gums of a series.

The term RSD as used herein is short for the relative standard deviation, which within this present field is used to indicate the uniformity in content of non-DC sugar alcohols in a series of gum base free modules of the chewing gums. An analysis may be carried out on an array of 10 chewing gums of a series, wherein the content of the non-DC sugar alcohols in question is measured. From these values the RSD may be calculated through the standard formula of $$\text{RSD} = (\text{standard deviation of array } X) * 100\% / (\text{average of array } X).$$

In some cases, it may be most convenient to measure RSD of the amount of non-DC sugar alcohol particles indirectly. For example, the RSD of another ingredient may be used as an indicator for the amount of non-DC sugar alcohol particles, as segregation affects the whole composition of the chewing gum or module in question.

When attempting to obtain a high degree of even distribution of the non-DC areas, insufficient mixing may lead to uneven distribution, such as undesirable agglomeration of particles within certain parts of the chewing gum. Also, even if mixing very thoroughly the ingredients, an undesirable handling of the mixture from the mixing to a tableting machine may lead to segregation. For example, smaller particles may typically segregate to the bottom part of a container, thereby leading to different particle distributions for different chewing gums. Particularly when the different ingredients have different particle sizes, e.g. if non-DC sugar alcohol particles have a larger particle size compared to other ingredients, segregation may lead to different contents of non-DC sugar alcohols in different chewing gums. Yet, another aspect is that even storing a thoroughly mixed composition for too long may lead to segregation.

On the other hand, a measure of having obtained even distribution of non-DC areas in at least one module of the chewing gum may be that a series of at least 10 of the chewing gums holds a relative standard deviation (RSD) below 10% with respect to the non-DC sugar alcohol content.

In is noted that the term segregation as used herein would be known to the skilled person to mean the separation of a mixture according to similarity, typically size. This may in the present context be a problem when handling a mixture comprising very different sizes of particles, e.g. in a hopper for holding and feeding the composition via a feeding mechanism to a die cavity.

Particularly, when including an active ingredient in the chewing gum, having a low RSD on the content of such active ingredients is highly desirable.

In an embodiment of the invention, the non-DC particles are providing the chewing gum with a plurality of discrete non-DC areas, where the non-DC areas are homogenously distributed in the chewing gum or at least one module of the chewing gum.

One advantage of the above embodiment may be that the homogenous distribution of the non-DC areas promotes an effective disintegration of the module upon mastication, e.g. due to lower mechanical strength contribution from the non-DC sugar alcohol particles, thereby facilitating effective contacting of the resulting mastication fragments formed by the mastication with saliva, again increasing dissolving a module or part of the chewing gum. Also, the homogenous distribution of the non-DC areas promotes a high number of mastication fragments with non-DC sugar alcohols, which again effectively promotes salivation. Thus, a synergy between utilization of non-DC sugar alcohol particles as a disintegration promoter due to the lower mechanical strength and also as a salivation promoter in combination with the homogenous distribution to facilitate effect dispersion of mastication fragments in the oral cavity upon mastication.

In an embodiment of the invention, the non-DC particles provides the chewing gum with a plurality of discrete non-DC areas, where the non-DC areas are homogenously distributed in a gum base free module of the chewing gum.

In an embodiment of the invention, at least 10% by weight of said population of particles have a particles size below 250 μm, and wherein at least 30% by weight of said population of particles have a particles size above 500 μm.

According to an embodiment of the invention, the population of particles have a particle size distribution with a full width at half maximum (FWHM) of at least 100 μm.

Particularly when having a broad particle size distribution of the population of particles, it was surprising to the inventor that even distribution of the non-DC areas could be accomplished. Typically, when having a broad particle size distribution, such as when having a width from the 10% quantile to the 90% quantile greater than 30% of the mean value, associated compositions are considered vulnerable to segregation. However, according to an embodiment of the invention, the non-DC areas are evenly distributed in at least one module of the chewing gum and may have amounts of non-DC sugar alcohol particles between a series of at least 10 of the chewing gums holding a relative standard deviation (RSD) below 10%.

According to an embodiment of the invention, the non-DC sugar alcohol particles have an average non-DC sugar alcohol particle size at least 50 μm larger than an average DC particle size of the DC sugar alcohol particles.

In an embodiment of the invention, the non-DC sugar alcohol particles are selected from non-DC particles of erythritol, maltitol, xylitol, isomalt, lactitol, mannitol, and combinations thereof.

One advantage of the above embodiment may be that a desirable induced saliva generation is obtained.

According to an embodiment of the invention, the non-DC sugar alcohol particles consist of sugar alcohols selected from erythritol, maltitol, xylitol, isomalt, lactitol, mannitol, and combinations thereof.

In an embodiment of the invention, the non-DC sugar alcohol particles are selected from non-DC particles of erythritol, maltitol, xylitol, isomalt, and combinations thereof.

One advantage of the above embodiment may be that a desirable induced saliva generation is obtained.

In an embodiment of the invention, the non-DC sugar alcohol particles are selected from non-DC particles of erythritol, maltitol, xylitol, and combinations thereof.

One advantage of the above embodiment may be that a desirable induced saliva generation is obtained. Also, when a cooling sensation is desirable, having non-DC sugar alcohol particles comprising or consisting of erythritol, xylitol, or combinations thereof advantageous.

In an embodiment of the invention, the non-DC sugar alcohol particles are non-DC erythritol particles.

One advantage of the above embodiment may be that a desirable induced saliva generation is obtained, together with a cooling sensation.

In an embodiment of the invention, the non-DC sugar alcohol particles are non-DC xylitol particles.

One advantage of the above embodiment may be that a desirable induced saliva generation is obtained, together with a cooling sensation.

In an embodiment of the invention, the chewing gum comprises said non-DC sugar alcohol particles in an amount of at least 10% by weight of the chewing gum.

In an embodiment of the invention, the DC sugar alcohol particles comprises sugar alcohols selected from DC particles of sorbitol, erythritol, xylitol, lactitol, maltitol, mannitol, isomalt, and combinations thereof.

Sorbitol is an example of a sugar alcohol, which is considered DC grade, when provided as particles consisting of sorbitol, i.e. in its pure form. On the other hand, several other sugar alcohols are considered non-DC grade if providing them as particles consisting of the specific sugar alcohol. Therefore, such non-DC sugar alcohols are conventionally processed into DC grade sugar alcohols, e.g. by granulating them with e.g. a binder.

Examples of trade grades of DC sugar alcohols include sorbitol particles provided as e.g. Neosorb® P 300 DC from Roquette, mannitol particles provided as e.g. Pearlitol® 300DC or Pearlitol 200 SD from Roquette, maltitol provided as e.g. SweetPearl® P 300 DC, xylitol provided as e.g. Xylisorb® 200 DC or Xylitab 200 from Dupont.

In an embodiment of the invention, the chewing gum comprises said DC sugar alcohol particles in an amount of at least 10% by weight of the chewing gum.

According to an embodiment of the invention, said population of particles comprises DC sugar alcohol particles in an amount of at least 10% by weight.

According to an embodiment of the invention, the first module comprises DC sugar alcohol particles in an amount of at least 10% by weight.

In an embodiment of the invention, the second module comprises DC sugar alcohol particles in an amount of at least 30% by weight of the second module In an embodiment of the invention, the second module comprises DC sugar alcohol particles in an amount of at least 50% by weight of the second module.

In an embodiment of the invention the DC sugar alcohol particles in the second module are selected from DC particles of sorbitol, erythritol, xylitol, lactitol, maltitol, mannitol, isomalt, and combinations thereof.

In an embodiment of the invention, friability of the chewing gum is less than 3%, such as less than 2.5%, such as less than 2%, such as less than 1.5%, such as less than 1.0%, wherein friability is measured according to European Pharmacopoeia 9.1, test method 2.9.7. by using a pharmaceutical friability-tester PTF 10E from Pharma Test.

One advantage of the above embodiment may be that a chewing gum with a relatively high mechanical stability is obtained, while at the same time having the desirable mouthfeel of the invention.

According to an embodiment of the invention, friability of the chewing gum is between 0.2% and 3%, such as between 0.2% and 2%, wherein friability is measured according to European Pharmacopoeia 9.1, test method 2.9.7. by using a pharmaceutical friability-tester PTF 10E from Pharma Test.

In an embodiment of the invention, the chewing gum comprises one or more binders other than binders forming part of the DC sugar alcohol particles in an amount of 0.1 to 6% by weight of the chewing gum.

Suitable binders include Gum Arabic, Methyl Cellulose, Liquid glucose, Tragacanth, Ethyl Cellulose, Gelatin, Hydroxy Propyl Methyl Cellulose (HPMC), Starches, Hydroxy Propyl Cellulose (HPC), Pregelatinized Starch, Sodium Carboxy Methyl Cellulose (NaCMC), Alginic Acid, Polyvinyl Pyrrolidone (PVP), Maltodextrine (MD); Cellulose, Polyethylene Glycol (PEG), Polyvinyl Alcohols, Polymethacrylates, Copovidone or Microcrystalline Cellulose (MCC), alone or in combination.

According to an embodiment of the invention, the one or more binders comprises one or more cellulose binders.

In an embodiment of the invention the one or more binders comprises microcrystalline cellulose (MCC), hydroxypropyl cellulose (HPC) or hydroxypropylmethyl cellulose (HPMC) or any combination thereof.

In an embodiment of the invention the chewing gum comprises hydroxypropyl cellulose (HPC) binder in the amount of 0.1 to 6% by weight of the chewing gum, such as 0.1 to 5%, such as 0.1 to 4%, such as 0.1 to 3%, such as 0.1 to 2% by weight of the chewing gum.

HPC may be applied as a particular attractive binder. Thus, this binder, when used with non-DC sugar alcohols such as erythritol, exhibits an advantageous sensory experience when compared to other well-known binders, such as carboxymethylcellulose CMC. In particular, the usage level of HPC is lower than 4% by weight of the chewing gum is advantageous, such as 0.1 to 3%, such as 0.1 to 2% by weight of the chewing gum.

In an embodiment of the invention the non-DC sugar alcohol particles are particles that are not granulated, and the one or more binders are present as separate components in the tablet.

In an embodiment of the invention the non-DC sugar alcohol particles are particles consisting of the sugar alcohol and the particles are not pre-granulated together with the one or more binders that are present in the tablet as separate components.

It is noted that the use of binders as particles separate from the non-DC sugar alcohol particles does not compromise the advantageous sensory properties even when applying a firm pressure tableting force, whereas the granulation with the binder to the sugar alcohol clearly reduces the desired sensory properties.

High intensity artificial sweetening agents can also be used alone or in combination with the above sweeteners. Preferred high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided using another tablet component such as a resinous compound.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (preferably from about 0.02 to about 8% by weight). When carriers used for encapsulation are included, the usage level of the encapsulated sweetener will be proportionately higher. Combinations of sugar and/or non-sugar sweeteners may be used in the chewing gum formulation.

In an embodiment of the invention, the chewing gum has a weight ratio between said non-DC sugar alcohol particles and said DC sugar alcohol particles, which is between 0.3 and 1.2, such as between 0.5 and 1.2, such as between 0.7 and 1.1.

The weight ratio between non-DC sugar alcohol particles and DC sugar alcohol particles have proven significant according to an embodiment of the invention in the sense that a relatively high amount of non-DC sugar alcohol particles must be present in order to obtain the mouthfeel and taste obtained through the invention. However, this taste and mouthfeel also resides in the DC sugar alcohol particles. An example of such DC sugar alcohol particle is DC grade xylitol, which, together with the non-DC sugar alcohol particles may provide a mouthfeel which is unique and very attractive to test panels.

The weight ratio between non-DC sugar alcohol particles and DC sugar alcohol particles have proven significant as mentioned above in relation to the direct sensation and mouthfeel experienced by the user but is has moreover addressed the challenge in relation to mouthfeel when DC sugar alcohol particles crumbles during the initial chew. The mechanical stability of the chewing gum is much desired when the chewing gum is in its non-chewed form, but a fast disintegration and dissolving of a part of the chewing gum is desirable when the chewing gum is chewed due to the fact that user of the chewing gum dislike a sandy mouthfeel induced through small hard-pressed crumbles of DC sugar alcohol. The use of a very high amount of non-DC sugar alcohol particles will facilitate a perceived fast dissolving and disintegration of a part of the chewing gum after the initial chews.

According to an embodiment of the invention the chewing gum has a weight ratio between said non-DC sugar alcohol particles and said DC sugar alcohol particles, which is greater than 0.3, such as greater than 0.5, such as greater than 0.7.

According to an embodiment of the invention the chewing gum has a weight ratio between said non-DC sugar alcohol particles and said DC sugar alcohol particles, which is smaller than 1.2, such as smaller than 1.1.

The weight ratio between non-DC sugar alcohol particles and DC sugar alcohol particles is important for the purpose of obtaining an advantageous taste and mouthfeel. By having an upper limit of this weight ratio, the chewer will moreover also experience a desirable crunch sensation when starting masticating the tablet, the crunch being obtained through the use of substantial amounts of DC sugar alcohol particles and the non-DC sugar alcohol particles.

According to an embodiment of the invention, the chewing gum comprises the non-DC sugar alcohol particles in an amount of greater than 0.3 gram.

According to an embodiment of the invention, the weight of non-DC sugar alcohol particles contained in the chewing gum is greater than greater than 0.4 gram, such as greater than 0.5 gram, such as greater than 0.6 gram, such as greater than 0.7 gram, such as greater than 0.8 gram, such as greater than 0.9 gram, such as greater than 1.0 gram.

According to a further embodiment of the invention, the amount of non-DC sugar alcohol particles is relatively high. It is in particular high when considering that the non-DC sugar alcohol in conventional sense is not regarded attractive for compression, but the mouthfeel and salivation perceived by the user is there improved significantly, when compared to low amounts or the same amounts of DC sugar alcohol.

According to an embodiment of the invention, the chewing gum comprises the non-DC sugar alcohol particles in an amount of less than 3.0 gram, such as less than 2.0 gram, such as less than 1.5 gram.

In an embodiment of the invention wherein the chewing gum has a weight of between 0.5 and 4.0 grams.

In an embodiment of the invention, saliva generation upon mastication of the chewing gum is induced compared to a chewing gum without non-DC sugar alcohol particles.

In an embodiment of the invention, saliva generation upon mastication of the chewing gum is induced compared to a chewing gum where the discrete areas are based on DC sugar alcohol particles.

In an embodiment of the invention, the chewing gum generates more than 1.0 mL saliva per 10 seconds within 30 seconds from onset of mastication.

In an embodiment of the invention, the chewing gum generates more than 0.5 mL saliva per 10 seconds within a period from 30 to 90 seconds from onset of mastication.

In an embodiment of the invention, the chewing gum generates more than 0.2 mL saliva per 10 seconds within a period from 90 to 180 seconds from onset of mastication.

In an embodiment of the invention, the chewing gum generates more than 0.2 mL saliva per 10 seconds within a period from 180 to 300 seconds from onset of mastication.

In an embodiment of the invention, the chewing gum comprises flavor.

The amount of flavor may e.g. be from 0.1 to about 10% by weight of the tablet, such as 0.1 to about 6% by weight of the tablet.

Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), chili, cinnamon redhots, cotton candy, circus cotton candy, clove, coconut, coffee, clear coffee, double chocolate, energy cow, ginger, glutamate, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

In an embodiment of the invention, the chewing gum comprises an active ingredient.

According to an embodiment of the invention the active ingredient is included in the population of particles.

In an embodiment of the invention, the chewing gum comprises an active pharmaceutical ingredient.

According to an embodiment of the invention the active pharmaceutical ingredient is included in the population of particles.

In an embodiment of the invention, the population of particles comprises particles comprising gum base, and wherein the chewing gum is designed to be masticated into a coherent residual containing water-insoluble components.

The application of gum in the present context may invoke a delay of release for active ingredients and this may again promote the buccal and upper throat absorption of active pharmaceutical ingredient when this is released from the chewing gum during mastication.

In an embodiment of the invention, the chewing gum contains particles comprising gum base, and wherein the gum base comprises at least 5% by weight of elastomer.

The specific use of a relatively high proportion of elastomer in the gum base may effectively be used for modification of the release of active ingredients in terms of time and amount and the elastomer may also provide robust structure of the tablet facilitating that it is chewed into a coherent residual containing water-insoluble components. Some active ingredient may risk invoking disintegration of the residual whereas an elastomer may increase the coherence and compensate for the aggressive active ingredients.

In an embodiment of the invention the gum base comprises at least 10% by weight of elastomer.

In an embodiment of the invention the gum base comprises at least 15% by weight of elastomer.

In an embodiment of the invention the gum base comprises between 15% and 25% by weight of elastomer.

In an embodiment of the invention the gum base comprises between 17% and 23% by weight of elastomer.

In an embodiment of the invention, one of the modules of the chewing gum is free of gum base.

In an embodiment of the invention, the chewing gum is for use in buccal absorption of active ingredients.

Moreover, the invention relates to a medical device in tablet form comprising a population of particles, the population of particles comprising a) directly compressible (DC) sugar alcohol particles, b) non-directly compressible (non-DC) sugar alcohol particles and c) particles comprising gum base, the medical device for use in the alleviation or treatment of xerostomia.

Moreover, the invention relates to a tablet form comprising a population of particles, the population of particles comprising a) directly compressible (DC) sugar alcohol particles, b) non-directly compressible (non-DC) sugar alcohol particles and c) particles comprising gum base, the medical device for use in treatment or alleviation of dysphagia.

Moreover, the invention relates to a tableted chewing gum suitable for active pharmaceutical ingredients, the chewing gum comprising a) directly compressible (DC) sugar alcohol particles and b) non-directly compressible (non-DC) sugar alcohol particles comprised in a first module and c) particles comprising gum base comprised in a second module, the first module being designed to turn into liquid within 20 seconds of mastication.

Moreover, the invention relates to a tableted chewing gum suitable for active pharmaceutical ingredients, the chewing gum comprising a) directly compressible (DC) sugar alcohol particles and b) non-directly compressible (non-DC) sugar alcohol particles comprised in a first module and c) particles comprising gum base comprised in a second module, the first module being designed dissolve within 20 seconds of mastication.

Moreover, the invention relates to a method suitable for delivering active pharmaceutical ingredients, the method comprising the steps of:

i) providing a tableted chewing gum comprising a population of particles, the population of particles comprising a) directly compressible (DC) sugar alcohol particles, b) non-directly compressible (non-DC) sugar alcohol particles and c) particles comprising gum base, the gum base comprising at least 5% by weight of elastomer, and ii) masticating the chewing gum to release water soluble ingredients into saliva.

In an embodiment of the invention, the step ii) of masticating the chewing gum involves masticating the chewing gum to release water soluble ingredients into saliva induced by a plurality of discrete non-DC areas in the chewing gum.

In an embodiment of the invention, the step ii) of masticating the chewing gum involves releasing at least 50% by weight of the active ingredient within 20 seconds from onset of mastication.

In an embodiment of the invention, the chewing gum comprises an oral care agent in the amount of at least 0.1% by weight of the chewing gum.

In an embodiment of the invention, the chewing gum comprises tooth paste in the amount of at least 0.1% by weight of the chewing gum.

In an embodiment of the invention the chewing gum comprises dentifrice in the amount of at least 0.1% by weight of the chewing gum.

In an embodiment of the invention the chewing gum comprises dentifrice in the amount of at least 0.1% to 25% by weight of the chewing gum excluding abrasive.

Dentifrice will typically comprise at least one of the below active ingredients targeting oral care.

In an embodiment of the invention the active ingredient comprises one or more oral care agents.

In an embodiment of the invention the active ingredient comprises one or more anti-plaque agent.

Anti-plaque agents include fluoride ion sources. Anti-plaque agents are any substance which by itself acts to inhibit the accumulation of bacterial deposits on the surfaces of the oral cavity. Examples include xylitol and other anti-microbial agents. The inhibition effects of the xylitol on oral microbes may have better effect when used in conjunction with an extract since the extract is also acting to disable the microbes.

Typical examples of active ingredients that are particularly desirable from considerations of anti-plaque effectiveness, safety and formulation are:

Naficillin, oxacillin, vancomycin, clindamycin, erythromycin, trimethoprim-sulphamethoxazole, rifampin, ciprofloxacin, broad spectrum penicillin, amoxicillin, gentamicin, ceftriazoxone, cefotaxime, chloramphenicol, clavunate, sulbactam, probenecid, doxycycline, spectinomycin, cefixime, penicillin G, minocycline, .beta.-lactamase inhibitors; meziocillin, piperacillin, aztreonam, norfloxacin, trimethoprim, ceftazidime, dapsone. Halogenated diphenyl ethers, e.g. 2',4,4'-trichloro-2-hydroxydiphenyl ether (Triclosan), 2,2'-dihydroxy-5,5'-dibromo-diphenyl ether. Haloqenated salicylanilides, e.g. 4',5-dibromosalicylanilide, 3,4',5-trichloro-salicylanilide, 3,4',5-tribromo-salicylanilide, 2,3,3',5-tetrachloro-salicylanilide, 3,3,3',5-tetrachloro-salicylanilide, 3,5-dibromo-3'-trifluoromethyl-salicylanilide, 5-n-octanoyl-3'-trifluoromethyl-salicylanilide, 3,5-dibromo-4'-trifluoromethyl-salicylanilide, 3,5-dibromo-3'-trifluoromethyl-salicylanilide (Flurophene). Benzoic esters, e.g. methyl-p-hydroxybenzoic ester, ethyl-p-hydroxybenzoic ester, propyl-p-hydroxybenzoic ester, butyl-p-hydroxybenzoic ester. Halogenated carbanilides, e.g. 3,4,4'-trichlorocarbanilide, 3-trifluoromethyl-4,4'-dichlorocarbanilide, or 3,3,4'-trichlorocarbanilide. Phenolic compounds (including phenol and its homologs, mono- and poly-alkyl and aromatic halophenol and their homologs), e.g. phenol, 2-methyl-phenol, 3-methyl-phenol, 4-methyl-phenol, 4-ethyl-phenol, 2,4-dimethyl-phenol, 2,5-dimethyl-phenol, 3,4-dimethyl-phenol, 2,6-dimethyl-phenol, 4-n-propyl-phenol, 4-n-butyl-phenol, 4-n-amyl-phenol, 4-tert-amyl-phenol, 4-n-hexyl-phenol, 4-n-heptyl-phenol, 2-methoxy-4-(2-propenyl)-phenol (Eugenol), 2-isopropyl-5-methyl-phenol (Thymol), mono- and poly-alkyl- and aralkyl-halophenols, methyl-p-chlorphenol, ethyl-p-chlorphenol, n-propyl-p-chlorophenol, n-butyl-p-chlorophenol, n-amyl-p-chlorophenol, sec-amyl-p-chlorophenol, n-hexyl-p-chlorophenol, cyclohexyl-p-chlorophenol, n-heptyl-p-chlorophenol, n-octyl-p-chlorophenol, o-chlorophenol, methyl-o-chlorophenol, ethyl-o-chlorophenol, n-propyl-o-chlorophenol, n-butyl-o-chlorophenol, n-amyl-o-chlorophenol, tert-amyl-o-chlorophenol, n-hexyl-o-chlorophenol, n-heptyl-o-chloropenol, p-chlorophenol, o-benzyl-p-chlorophenol, o-benzyl-m-methyl-p-chlorophenol, o-b enzyl-m,m-dimethyl-p-chlorophenol, o-phenylethyl-p-chlorophenol, o-phenylethyl-m-methyl-p-chlorophenol, 3-methyl-p-chlorophenol, 3,5-dimethyl-p-chlorophenol, 6-ethyl-3-methyl-p-chlorophenol, 6-n-propyl-3-methyl-p-chlorophenol, 6-isopropyl-3-methyl-p-chlorophenol, 2-ethyl-3,5-dimethyl-p-chlorophenol, 6-sec-butyl-3-methyl-p-chlorophenol, 2-isopropyl-3,5-dimethyl-p-chlorophenol, 6-diethylmethyl-3-methyl-p-chlorophenol, 6-iso-propyl-2-ethyl-3-methyl-p-chlorophenol, 2-sec-amyl-3,5-dimethyl-p-chlorophenol, 2-diethylmethyl-3,5-dimethyl-p-chlorophenol, 6-sec-octyl-3-methyl-p-chlorophenol, p-bromophenol, methyl-p-bromophenol, ethyl-p-bromophenol, n-propyl-p-bromophenol, n-butyl-p-bromophenol, n-amyl-p-bromophenol, sec-amyl-p-bromophenol, n-hexyl-p-bromophenol, cyclohexyl-p-bromophenol, o-bromophenol, tert-amyl-o-bromophenol, n-hexyl-o-bromophenol, n-propyl-m,m-dimethyl-o-bromophenol, 2-phenyl-phenol, 4-chloro-2-methyl-phenol, 4-chloro-3-methyl-phenol, 4-chloro-3,5-dimethyl-phenol, 2,4-dichloro-3,5-dimethyl-phenol, 3,4,5,6-tetrabromo-2-methylphenol, 5-methyl-2-pentylphenol 4-isopropyl-3-methylphenol 5-chloro-2-hydroxydiphenyl-methane. Resorcinol and its derivatives, e.g. resorcinol, methyl-resorcinol, ethyl-resorcinol, n-propyl-resorcinol, n-butyl-resorcinol, n-amyl-resorcinol, n-hexyl-resorcinol, n-heptyl-resorcinol, n-octyl-resorcinol, n-nonyl-resorcinol, phenyl-resorcinol, benzyl-resorcinol, phenylethyl-resorcinol, phenylpropyl-resorcinol, p-chlorobenzyl-resorcinol, 5-chloro-2,4-dihydroxydiphenyl-methane, 4'-chloro-2,4-dihydroxydiphenyl-methane, 5-bromo-2,4-dihydroxydiphenyl-methane, 4"-bromo-2,4-dihydroxydiphenyl-methane. Bisphenolic compounds, e.g. bisphenol A, 2,2'-methylene-bis-(4-chlorophenol), 2,2'-methylene-bis-(3,4,6-trichlorophenol) (hexachlorophene), 2,2'-methylene-bis-(4-chloro-6-bromophenol), bis-(2-hydroxy-3,5-dichlorophenyl)-sulfide, bis-(2-hydroxy-5-chlorobenzyl)-sulfide.

Illustrative of polyphosphate compounds with plaque-inhibiting properties are dialkali metal and tetraalkali metal pyrophosphate and mixtures thereof in a hydrated or unhydrated form. Illustrative of pyrophosphate salts are Na2H2P2O7, Na4P2O7 and K4P2O7. Other suitable polyphosphates include hydrated or unhydrated alkali metal tripolyphosphates such as Na5P3O10 and K5P3O10.

In an embodiment of the invention the active ingredient comprises one or more Anti-gingivitis agents.

Anti-gingivitis agents can be antiinflammatory agents, such as salicylic acid derivatives (e.g. aspirin), paraminophenol derivative (e.g. acetaminophen), indole and indene acetic acids (indo-methacin, sulindac and etodalac), heteroaryl acetic acids (tolmetin, diclofenac and ketorolac), aryl propionic acid derivatives (ibuprofen, naproxen, ketoprofen, fenopren, oxaprozine), anthranilic acids-(mefenamic acid, meclofenamic acid), enolic acids (piroxicam, tenoxicam, phenylbutazone and oxyphenthatrazone), lactic acid bacteria (LAB), Osteopontin (ONP), IG-Lyt, hexefine, Aloe Vera, chlorhexedine, myrrh, or sage.

Anti-gingivitis agents also comprise psychotherapeutic agents, such as thorazine, serentil, mellaril, millazine, tindal, permitil, prolixin, trilafon, stelazine, suprazine, taractan, navan, clozaril, haldol, halperon, loxitane, moban, orap, risperdal, alprazolam, chlordiaepoxide, clonezepam, clorezepate, diazepam, halazepam, lorazepam, oxazepam, prazepam, buspirone, elvavil, anafranil, adapin, sinequan, tofranil, surmontil, asendin, norpramin, pertofrane, ludiomil, pamelor, vivactil, prozac, luvox, paxil, zoloft, effexor, welibutrin, serzone, desyrel, nardil, parnate, or eldepryl.

In an embodiment of the invention, the active ingredient comprises one or more dental cosmetic ingredients.

A dental cosmetic ingredient includes a whitening agent. These are conveniently selected from teeth colour modifying substances that may be considered among the oral care actives useful in the chewing gum according to the invention. These substances are suitable for modifying the colour of the teeth to satisfy the consumer such as those listed in the CTFA Cosmetic Ingredient Handbook, 3.sup.rd Edition, Cosmetic and Fragrances Association Inc., Washington D.C. (1982), incorporated herein by reference. Specific examples include talc, mica, magnesium carbonate, calcium carbonate, calcium pyrophosphate, Baking soda, Icelandic moss, bamboo, sodium hexa-metaphosphate, magnesium silicate, aluminium magnesium carbonate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures thereof. Typical levels are from about 0.05% to about 20%, preferably from about 0.1% to about 15% and most preferably from about 0.25% to about 10%, by weight, of the composition.

Whitening agents for use herein may also comprise materials that remove or bleach intrinsic or extrinsic stains on or in tooth surfaces. Such substances are selected from the group consisting of the peroxides, metal chlorites, perborates, percarbonates, peroxyacids, persulphates, and combinations thereof. Suitable peroxide compounds include hydrogen peroxide, urea peroxide, calcium peroxide, carbamide peroxide and mixtures thereof. Suitable metal chlorites include calcium chlorite, barium chlorite, magnesium chlorite, lithium chlorite, sodium chlorite and potassium chlorite. Additional bleaching substances may be hypochlorite, and chlorine dioxide. A preferred percarbonate is sodium percarbonate. Preferred persulphates are oxones. The content of these substances is dependent on the available oxygen or chlorine.

In an embodiment of the invention the active ingredient comprises one or more abrasives.

Within the scope of the invention, the chewing gum may comprise abrasive. Typical materials include silica gels and precipitates, aluminas, phosphates, and mixtures thereof. Specific examples include dicalcium orthophosphate dihydrate, calcium pyrophosphate, Bamboo, tricalcium phosphate, hydrated alumina, beta calcium pyrophosphate, calcium carbonate, sodium polymetaphosphate, sodium hexametaphosphate, Calgen, Giltex, Quadrafos, Hagan phosphate, micromet, calcium phosphate dibasic, calcium monohydrogen phosphate, dicalcium orthophosphate secondary calcium phosphate, carbonic acid calcium salt, cacti, calcichew, calcidia, citrical, aragonite, calcite, valerite, aluminum oxide, alumina, silicon dioxide, silica, silicic anhydride, and resinous abrasive materials such as particulate condensation products of urea and formaldehyde and others such as disclosed in U.S. Pat. No. 3,070,510. Mixtures of polishing agents can also be used.

The silica polishing materials generally have an average particle size ranging between about 0.1 to about 30 microns; and preferably from about 5 to about 15 microns. The polishing agent can be precipitated silica or silica gels, such as the silica xerogels described in U.S. Pat. No. 3,538,230 or in U.S. Pat. No. 3,862,307. Preferred are the silica xerogels marketed under the name "Syloid" by the W. R. Grace and Company, Davison Chemical Division. Also preferred are the precipitated silica materials such as those marketed by the J. M. Huber Corporation under the trade name "Zeodent", particularly the silica carrying the designation "Zeodent 119". The types of silica dental polishing agents useful in the chewing gum of the present invention are described in more details in U.S. Pat. No. 4,340,583. The polishing agents in the chewing gum according to the invention is generally present in the range from about 6% to about 70%, preferably from about 10% to about 50%, by weight of the chewing gum.

In an embodiment of the invention the chewing gum comprises one of more of the following active ingredients anti-plaque agent, anti-gingivitis, dental cosmetic ingredient and/or abrasive in the amount of 0.1% to 35%, such as from 1% to 25% or such as from about 5% to about 10%, by weight of the chewing gum.

The content of these oral care ingredients in the chewing gum according to the invention is generally in the range from about 0.1% to about 35%, preferably from about 1% to about 25% and most preferably from about 5% to about 10%, by weight of the chewing gum.

BRIEF DESCRIPTION OF THE DRAWINGS

For a more complete understanding, reference is now made to the following description taken in conjunction with the accompanying Drawings in which.

DETAILED DESCRIPTION

Figure 1A:
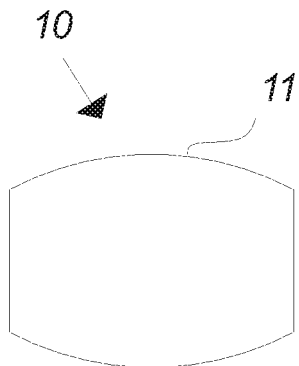
FIGS. 1A and 1B illustrate an embodiment of the invention.

Referring now to the drawings, wherein like reference numbers are used herein to designate like elements throughout, the various views and embodiments are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

As used herein the term "tableted chewing gum" is considered as a chewing gum formed by tableting, i.e. compression of a particle composition, comprising the mentioned population of particles. Thus, the chewing gum is considered a compressed chewing gum formed by a plurality of particles. The tablet is suitable for delivery of active pharmaceutical ingredients, or other active ingredients. Attractive ingredients include compounds for oral care or nutraceuticals. The tableted chewing gum may also be referred to as a gum or chewing gum tablet. In the present context it should be noted that a tablet or an oral tablet, even without designating it specifically, will refer to a chewing gum unless otherwise stated.

In the present context the phrase "population of particles" refers to a statistical population of particles. The population of particles may be characterized by a number of different parameters, e.g. statistical parameters such as distribution of particles, average particle size, particle size distribution width, etc. The population of particles may have subpopulations, such as DC sugar alcohol particles, non-DC sugar alcohol particles, or in some embodiments particles comprising gum base. The phrasing "population of particles" may in an embodiment of the invention be provided as a plurality of tableted particles and where the population of particles are tableted in one module or it may refer to a population of particles where some of the particles are tableted into one module and other particles are tableted into another module.

In the present context, the term "non-DC areas" refers to small volumes or spaces formed during tableting from the non-DC particles of non-DC sugar alcohol. Moreover, each of the non-DC areas may be composed of a single non-DC sugar alcohol particle, or may comprise several non-DC sugar alcohol particles. When the non-DC areas are distinct, i.e. not diffuse, the non-DC areas may be evenly distributed in the tablet, or at least one module thereof when the tablet comprises two or more modules. In such embodiments, where the non-DC areas are evenly distributed in in the tablet, or at least one module thereof, the non-DC areas may thus facilitate an even saliva generation in the mouth upon mastication.

The term "non-DC sugar alcohol particles" refer to particles of non-directly compressible (non-DC) sugar alcohol. It is noted that the terms "non-DC sugar alcohol particles" and "non-DC particles" are used interchangeably. In the present context, the non-DC sugar alcohol particles refer to particles which have not been preprocessed by granulation with e.g. other sugar alcohols or binders for the purpose of obtaining so-called direct compressible particles (DC). Thus, non-DC sugar alcohol particles are considered as particles consisting of non-DC sugar alcohol(s), often consisting of a single non-DC sugar alcohol.

The term "DC sugar alcohol particles" refer to particles of direct compressible (DC) sugar alcohol. It is noted that the terms "DC sugar alcohol particles" and "DC particles" are used interchangeably. DC sugar alcohol particles may be obtained e.g. as particles of sugar alcohols having DC grade by nature, e.g. sorbitol, or by granulating non-DC sugar alcohol with e.g. other sugar alcohols or binders for the purpose of obtaining so-called direct compressible particles (DC).

In the present context when the non-DC areas are referred to as "discrete" this signifies that the non-DC sugar alcohols are not continuously distributed, but present in the discrete areas corresponding to the discrete nature of the non-DC sugar alcohol particles.

In the present context, the term "suitable for active pharmaceutical ingredients" refers to the tablet as a suitable vehicle for e.g. inclusion and delivery of active pharmaceutical ingredients. However, it is noted that the tablet does not necessarily include active pharmaceutical ingredients or active ingredients.

The term "fast release" may in an embodiment refer to a large amount, such as at least 50% by weight of higher, of e.g. the active ingredient being released in a short time, such as within 20 seconds from onset of mastication, or shorter.

When referring to induced saliva generation, it is noted that this induced saliva generation exceeds any saliva generation without the use of the tablet of the invention. Particularly, in an embodiment the induced saliva generation exceeds saliva generation when using conventional tablets without non-DC areas. Then, induced saliva generation is increased over any saliva generation associated with conventional products, e.g. by comparing with a tablet without non-DC sugar alcohol particles, or with a tablet where the discrete areas are based on DC sugar alcohol particles.

When referring to induced saliva generation, the saliva generation is tested using the following method.

Test subjects abstain from eating and drinking at least 30 minutes before initiation of any test. Immediately before introducing of the tablet into the oral cavity, the test subject swallows. The test subject refrains from swallowing during the test. Immediately after introducing of the tablet into the oral cavity, the test subject starts masticating the tablet at a frequency of 1 chew per second for 30 seconds. 30 seconds after starting the test, the test subject discards saliva into a plastic cup, which is weighted. The test subject keeps the coherent residue in the mouth and continues chewing immediately after each discarding of saliva. Saliva is discarded also at 90 seconds after onset of mastication, at 180 seconds after onset of mastication, at 300 seconds after onset of mastication, at 420 seconds after onset of mastication, and at 600 seconds after onset of mastication. Saliva generation is noted as average amount of saliva per 10 seconds within the given time period.

As used herein, the term "particle size" refers to the average particle size as determined according to European Pharmacopoeia 9.1 when using test method 2.9.38 particle size distribution estimation by analytical sieving, unless otherwise specifically is mentioned.

In the present context, the term "taste masking" refers broadly to masking of any sensations perceived as unpleasant or other off-note tastes, but not necessarily confined to the classical five basic tastes. A typical example of off-note taste includes bitter taste. Also, metallic taste is another example of as an off-note taste.

As used herein the term "active ingredient" refers to a substance that is biologically active and has a physiological effect on the human body for the benefit of the human body or part thereof. Active ingredients include active pharmaceutical ingredients, but also other active substances such as nutraceuticals.

In the present context, the term "disintegrate" refers to is a process where the tablet falls apart or disintegrates in to smaller aggregates and as defined by European Pharmacopeia 2.9.1 "Disintegration of tablets and capsules". The time period of obtaining the desired disintegration, here less than 20 seconds.

In the present context the term "release" refers to the released substance being liberated from the water-soluble matrix. In some embodiments, the process of releasing a substance corresponds to the substance being dissolved in saliva.

As used herein the term "buccal absorption" refers to a substance diffusing across the oral mucosa from the oral cavity to enter the bloodstream.

As used herein the term "oral mucosa" refers to the mucous membrane in the oral cavity, i.e. in the mouth.

As used herein the term "gastrointestinal tract" refers to the part of the digestive system starting with the stomach and ending with the rectum, including the intestines. Thus, the mouth and esophagus are not considered part of the gastrointestinal tract for the purposes of the present application.

As used herein the term "throat" is considered front part of the neck, positioned in front of the vertebra, and including the pharynx and larynx.

Water-insoluble components in the present context typically refer to elastomer, natural or synthetic resins or other water-insoluble components such as water-insoluble softener or inorganic fillers.

As used herein, the phrase "tablet" refers to a tablet made by tableting in a tableting machine by pressing the tablet material to form the tablet. For example, the tablet material may be exposed to a punching means in a tableting machine, pressing e.g. granules and/or powder to a gathered mass of pressed material.

The tableting may be performed at a certain pressure, e.g. typically defined as compression force. Different types of tableting machines are known within the art, such as a rotary press device available by Fette.

As used herein, the phrase "granules" refers to entities made e.g. by granulation, and may typically contain a plurality of particles adhered together.

By the phrase "texture" is meant a qualitative measure of the visco-elastic properties of the tablet and of the overall mouth-feel experienced by the user during the mastication process. Thus, the term "texture" encompasses measurable quantities such as hardness and elasticity as well as more subjective parameters related to the chew-feel experienced by a user.

In some embodiments of the present invention, the gum base components comprise for example
 elastomer in the range of 1-15% by weight of the tablet,
 natural and/or synthetic resin in the range of 5-35% by weight of the tablet, and
 further other gum base components in the range of 5-30% by weight of the tablet.

It is evident, that the overall total amount of these above gum base components must be mutually adjusted in order to fit requirements with respect to tablet content of calcium carbonate, sweetener, flavor, etc.

In some embodiments of the present invention, the tablet comprises natural resins in an amount of 0.1 to 30%, such as 1 to 25%, such as 3 to 25% or 5 to 25%, by weight of the tablet.

In some embodiments of the present invention, the tablet comprises natural resins in an amount of at least 10% by weight of the tablet.

In some embodiments of the present invention, the tablet is free of natural resins.

In embodiments of the present invention, the tablet comprises synthetic resins in an amount of 0.1 to 30%, such as 1 to 25%, such as 3 to 25% or 5 to 25%, by weight of the tablet.

In embodiments of the present invention, the tablet comprises elastomer in an amount of at least 2% by weight of the tablet, such as at least 4% by weight of the tablet.

In embodiments of the present invention, the tablet comprises elastomer in an amount of less than 35% by weight of the tablet, such as less than about 25% by weight of the tablet, such as less than 20%, 15% or 10% by weight of the tablet.

In embodiments of the present invention, the tablet comprises one or more flavoring agents, preferably in powdered form, selected from the group consisting of essential oils, essences, extracts, powders, acids, coconut, coffee, chocolate, vanilla, grape fruit, orange, lime, menthol, liquorice, caramel aroma, honey aroma, peanut, walnut, cashew, hazelnut, almonds, pineapple, strawberry, raspberry, apple, pear, peach, apricot, blackberry, cherry, pineapple, plum essence, clove oil, bay oil, anise, thyme, cedar leaf oil, nutmeg, cinnamon, peppermint, wintergreen, spearmint, eucalyptus, mint, or any combination thereof.

In embodiments of the present invention, the tablet comprises one or more humectants, such as propylene glycol or glycerol.

In embodiments of the present invention, the tablet is provided with a coating.

In embodiments of the present invention, the tablet has a weight in the range of 0.1 to 10 grams, such as in the range of 0.5 to 4 grams or such as in the range of 1.5 to 2.5 grams.

According to an embodiment of the invention, the tablet may comprise filler. In embodiments of the present invention, the tablet comprises an additional filler in an amount of 0.1 to 40% by weight of the tablet.

Elastomers provide the rubbery, cohesive nature to the tablet, which varies depending on this ingredient's chemical structure and how it may be compounded with other ingredients. Elastomers suitable for use in the tablet of the present invention may include natural or synthetic types.

Elastomer plasticizers vary the firmness of the gum base components. Their specificity on elastomer inter-molecular interaction (plasticizing) along with their varying softening points cause varying degrees of finished tablet firmness and compatibility with other ingredients. This may be important when one wants to provide more elastomeric chain exposure to the alkane chains of the waxes. The elastomer plasticizers may typically be resins, such as synthetic resins and/or natural resins.

The elastomers employed in the tablet may vary depending upon various factors such as the desired texture of the coherent residual (i.e. the tablet after mastication) and the other components used in the formulation to make the tablet. The elastomer may be any water-insoluble polymer known in the art. Illustrative examples of suitable polymers in the tablet include both natural and synthetic elastomers. For example, those polymers which are suitable in the tablet include, without limitation, natural substances (of vegetable origin) such as chicle gum, natural rubber, crown gum, nispero, rosidinha, jelutong, perillo, niger gutta, tunu, balata, guttapercha, lechi capsi, sorva, gutta kay, and the like, and mixtures thereof. Examples of synthetic elastomers include, without limitation, styrene-butadiene copolymers (SBR), polyisobutylene, isobutylene-isoprene copolymers, polyethylene, and the like, and mixtures thereof.

Natural resins may be used according to the invention and may be natural rosin esters (also known as ester gums), including as examples glycerol esters of partially hydrogenated rosins, glycerol esters of polymerized rosins, glycerol esters of partially dimerized rosins, glycerol esters of tally oil rosins, pentaerythritol esters of partially hydrogenated rosins, methyl esters of rosins, partially hydrogenated methyl esters of rosins, pentaerythritol esters of rosins, synthetic resins such as terpene resins derived from alpha-pinene, beta-pinene, and/or d-limonene, and natural terpene resins.

In an embodiment of the invention a synthetic resin may include polyvinyl acetate (PVA) and/or vinyl acetate-vinyl laurate (VA-VL) copolymers In an embodiment of the invention, the tablet may comprise one or more components selected from the group consisting of bulk sweeteners, flavors, dry-binders, tableting aids, anti-caking agents, emulsifiers, antioxidants, enhancers, absorption enhancers, high intensity sweeteners, softeners, colors, or any combination thereof.

In an embodiment of the invention, the tablet comprises, apart from the DC and non-DC sugar alcohol particles, sweeteners, such as bulk sweeteners, sugar sweeteners, sugar substitute sweeteners, artificial sweeteners, high-intensity sweeteners, or any combination thereof.

Suitable bulk sweeteners include both sugar and non-sugar sweetening components.

Bulk sweeteners typically constitute from about 5 to about 95% by weight of the tablet, more typically about 20 to about 80% by weight such as 30 to 70% or 30 to 60% by weight of the tablet.

Useful sugar sweeteners are saccharide-containing components commonly known in the tablet art including, but not limited to, sucrose, dextrose, maltose, lactose, dextrins, trehalose, D-tagatose, dried invert sugar, fructose, levulose, galactose, corn syrup solids, and the like, alone or in combination.

As an example, sorbitol can be used as a non-sugar sweetener. Other useful non-sugar sweeteners include, but are not limited to, other sugar alcohols such as mannitol, xylitol, maltitol, isomalt, erythritol, lactitol and the like, alone or in combination.

Applicable but non-limiting non-DC sugar alcohols to be used within the scope of the invention includes:

Non DC Xylitol: Xivia C from Dupont
Non DC Isomalt: Isomalt GS from Beneo Paltinit
Non DC Mannitol: Pearlitol from Roquette
Non DC Maltitol: Maltisorb. P200 from Roquette
Non DC Erythritol: Zerose 16952 from Cargill High intensity artificial sweetening agents can also be used alone or in combination with the above sweeteners. For example, high intensity sweeteners include, but are not limited to sucralose, aspartame, salts of acesulfame, alitame, saccharin and its salts, cyclamic acid and its salts, glycyrrhizin, dihydrochalcones, thaumatin, monellin, stevioside (natural intensity sweetener) and the like, alone or in combination. In order to provide longer lasting sweetness and flavor perception, it may be desirable to encapsulate or otherwise control the release of at least a portion of the artificial sweeteners. Techniques such as wet granulation, wax granulation, spray drying, spray chilling, fluid bed coating, conservation, encapsulation in yeast cells and fiber extrusion may be used to achieve desired release characteristics. Encapsulation of sweetening agents can also be provided.

Usage level of the artificial sweetener will vary considerably and will depend on factors such as potency of the sweetener, rate of release, desired sweetness of the product, level and type of flavor used and cost considerations. Thus, the active level of artificial sweetener may vary from about 0.001 to about 8% by weight (such as from about 0.02 to about 8% by weight). When carriers used for encapsulation are included, the usage level of the encapsulated sweetener will be proportionally higher. Combinations of sugar and/or non-sugar sweeteners may be used in the tablet formulation.

A tablet according to the invention may, if desired, include one or more fillers/texturisers including as examples, magnesium, sodium sulphate, ground limestone, silicate compounds such as magnesium and aluminum silicate, kaolin and clay, aluminum oxide, silicium oxide, talc, titanium oxide, mono-, di- and tri-calcium phosphates, cellulose polymers, such as wood or microcrystalline cellulose (MCC), and combinations thereof.

A number of further tablet materials well known within the art may be applied within the scope of the present invention. Such components comprise but are not limited to waxes, fats, softeners, fillers, flavors, anti-oxidants, emulsifiers, colouring agents, binding agents and acidulants The granules or some of the granules may for example consist or largely comprise of gum base components and such granules may be manufactured by means of extrusion and under-water pelletizing.

The size of such granules of gum base components may according to the present invention be controlled by several factors such as opening sizes, the tablet composition, tablet temperature and pressure drop, if a die plate is used in the extruder. Due to an interaction between the pressurized tablet composition, temperature and friction in the openings of the die device, the average diameter of the produced granules are normally larger than the diameters of the openings in the die device. The relation between the diameters of the openings in the die device and the average diameters of granules produced from a specific tablet composition may be determined by the skilled person on basis of routine experiments.

According to the invention it is also possible to produce granules with different average diameters by making granules with one diameter, and subsequently mix the granules with different average diameters in desired proportions.

Although the openings of a die of an extruder device may have cross-sections of any desired shape, e.g. circular, oval, square etc., it is in some embodiments preferred that the die device comprises openings with substantially circular cross-section and diameters in the range of 0.1 to 1.3 mm. A first set of openings can e.g. have a first diameter in the range of 0.07 to 0.7 mm, such as in the range of 0.15 to 0.6 mm, and suitably in the range of 0.2 to 0.5 mm. A second set of openings can have a second diameter larger than said first diameter. The second diameter is conveniently in the range of 0.4 to 1.3 mm, such as in the range of 0.7 to 1.2 mm.

In some embodiments the tablet granulating system further comprises a drying device. Powder sweetener or talk may be added to the granules in a final drying step. The drying device can be a conventional centrifugal dryer or another suitable dryer e.g. a fluid bed dryer. The drying device can, for example, include a mixer. The powder sweetener may in an embodiment be sorbitol, which is mixed to the dried or partially dried granules. Minor amounts of residual moisture on the surface of the granules, e.g. 2% Wt. based on the total weight of the granules, may contribute to the adherence of the sorbitol powder to the surface of the granules. It is possible to use a conventional anti-agglomerating agent as e.g. talc, but sorbitol powder can function as an anti-agglomerating agent, and at the same time serves as sweetener. Although sorbitol is found to be most suitable, other bulk sweeteners based on polyols may also be suitable, e.g. mannitol, xylitol, hexa-resorcinol, maltitol, isomalt, erythriol, and lactitol.

In one embodiment the tablet granulating system according to the invention further comprises one or more sieves adapted for removing granules with an average diameter such as above 1.3 mm. The removal of larger granules improves a subsequent tableting process.

Examples of gum base components applicable for tablets of the present invention are described in the PCT/DK02/00461 and PCT/DK02/00462, hereby incorporated by reference.

The composition of gum base components, which are admixed with tablet ingredients as defined below, can vary substantially depending on the particular product to be prepared and on the desired masticatory and other sensory characteristics of the final product. However, typical ranges (weight %) of the above gum base components are:
elastomer in the range of 1-15% by weight of the tablet,
natural and/or synthetic resin in the range of 5-35% by weight of the tablet, and
further other gum base components in the range of 5-30% by weight of the tablet.

It is evident, that the overall total amount of these above gum base components must be mutually adjusted in order to fit requirements with respect to tablet content of calcium carbonate, sweetener, flavor, etc.

Granulates of gum base components may be manufactured according to conventional methods or e.g. those described in the PCT/DK02/00461 and PCT/DK02/00462, hereby incorporated by reference.

According to embodiments of the invention, encapsulated flavors or active ingredients may be added to the final blend of raw materials prior to compression.

Different methods of encapsulating flavors or active ingredients, which may both refer to flavors or active ingredients mixed into the raw materials to be compressed into the chewing gum may e.g. include spray drying, spray cooling, film coating, coascervation, Double emulsion method (Extrusion technology) or prilling.

Materials to be used for the above-mentioned encapsulation methods may e.g. include Gelatine, Wheat protein, Soya protein, Sodium caseinate, Caseine, Gum arabic, Mod. starch, Hydrolyzed starches (maltodextrines), Alginates, Pectin, Carregeenan, Xanthan gum, Locus bean gum, Chitosan, Bees wax, Candelilla wax, Carnauba wax, Hydrogenated vegetable oils, Zein and/or Sucrose.

Preferably, these ingredients should be added subsequent to any significant heating or mixing. In other words, the active ingredients should preferably be added immediately prior to the compression of the final tablet.

In one embodiment, the adding of active ingredients may be cautiously blended with pre-mixed gum base granulates and further ingredients such as the ingredients stipulated by the present claims, immediately prior to the final compression of the tablet.

For those active ingredients listed below, it should be noted that they are optional in the present invention unless specifically stated.

In one embodiment the tablet according to the invention comprises a pharmaceutically, cosmetically or biologically active substance. Examples of such active substances, a comprehensive list of which is found e.g. in WO 00/25598, which is incorporated herein by reference, include drugs, dietary supplements, antiseptic agents, pH adjusting agents, anti-smoking agents and substances for the care or treatment of the oral cavity and the teeth such as hydrogen peroxide and compounds capable of releasing urea during chewing. Examples of useful active substances in the form of antiseptics include salts and derivatives of guanidine and biguanidine (for instance chlorhexidine diacetate) and the following types of substances with limited water-solubility: quaternary ammonium compounds (e.g. ceramine, chloroxylenol, crystal violet, chloramine), aldehydes (e.g. paraformaldehyde), derivatives of dequaline, polynoxyline, phenols (e.g. thymol, p-chlorophenol, cresol), hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. also Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and salts, complexes and compounds of boron, barium, strontium, iron, calcium, zinc, (zinc acetate, zinc chloride, zinc gluconate), copper (copper chloride, copper sulphate), lead, silver, magnesium, sodium, potassium, lithium, molybdenum, vanadium should be included; other compositions for the care of mouth and teeth: for instance; salts, complexes and compounds containing fluorine (such as sodium fluoride, sodium monofluorophosphate, aminofluorides, stannous fluoride), phosphates, carbonates and selenium. Further active substances can be found in J. Dent. Res. Vol. 28 No. 2, pages 160-171, 1949.

Examples of active substances in the form of agents adjusting the pH in the oral cavity include: acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulphates or oxides of sodium, potassium, ammonium, magnesium or calcium, especially magnesium and calcium.

Active ingredients may comprise the below mentioned compounds or derivates thereof but are not limited thereto: Acetaminophen, Acetylsalicylic acid, Buprenorphine, Bromhexin, Celcoxib, Codeine, Diphenhydramin, Diclofenac, Etoricoxib, Ibuprofen, Indometacin, Ketoprofen, Lumiracoxib, Morphine, Naproxen, Oxycodon, Parecoxib, Piroxicam, Pseudoefedrin, Rofecoxib, Tenoxicam, Tramadol, Valdecoxib, Calciumcarbonat, Magaldrate, Disulfiram, Bupropion, Nicotine, Azithromycin, Clarithromycin, Clotrimazole, Erythromycin, Tetracycline, Granisetron, Ondansetron, Prometazin, Tropisetron, Brompheniramine, Ceterizin, leco-Ceterizin, Chlorcyclizine, Chlorpheniramin, Chlorpheniramin, Difenhydramine, Doxylamine, Fenofenadin, Guaifenesin, Loratidin, des-Loratidin, Phenyltoloxamine, Promethazin, Pyridamine, Terfenadin, Troxerutin, Methyldopa, Methylphenidate, Benzalcon. Chloride, Benzeth. Chloride, Cetylpyrid. Chloride, Chlorhexidine, Ecabet-sodium, Haloperidol, Allopurinol, Colchinine, Theophylline, Propanolol, Prednisolone, Prednisone, Fluoride, Urea, Actot, Glibenclamide, Glipizide, Metformin, Miglitol, Repaglinide, Rosiglitazone, Apomorfin, Cialis, Sildenafil, Vardenafil, Diphenoxylate, Simethicone, Cimetidine, Famotidine, Ranitidine, Ratinidine, cetrizin, Loratadine, Aspirin, Benzocaine, Dextrometorphan, Phenylpropanolamine, Pseudoephedrine, Cisapride, Domperidone, Metoclopramide, Acyclovir, Dioctylsulfosucc, Phenolphtalein, Almotriptan, Eletriptan, Ergotamine, Migea, Naratriptan, Rizatriptan, Sumatriptan, Zolmitriptan, Aluminum salts, Calcium salts, Ferro salts, Ag-salts, Zinc-salts, Amphotericin B, Chlorhexidine, Miconazole, Triamcinolonacetonid, Melatonine, Phenobarbitol, Caffeine, Benzodiazepiner, Hydroxyzine, Meprobamate, Phenothiazine, Buclizine, Brometazine, Cinnarizine, Cyclizine, Difenhydramine, Dimenhydrinate, Buflomedil, Amphetamine, Caffeine, Ephedrine, Orlistat, Phenylephedrine, Phenylpropanolamin, Pseudoephedrine, Sibutramin, Ketoconazole, Nitroglycerin, Nystatin, Progesterone, Testosterone, Vitamin B12, Vitamin C, Vitamin A, Vitamin D, Vitamin E, Pilocarpin, Aluminumaminoacetat, Cimetidine, Esomeprazole, Famotidine, Lansoprazole, Magnesiumoxide, Nizatide and or Ratinidine.

The invention is suitable for increased or accelerated release of active agents selected among the group of dietary supplements, oral and dental compositions, antiseptic agents, pH adjusting agents, anti-smoking agents, sweeteners, flavorings, aroma agents or drugs. Some of those will be described below.

The active agents to be used in connection with the present invention may be any substance desired to be released from the tablet. The active agents, for which a controlled and/or accelerated rate of release is desired, are primarily substances with a limited water-solubility, typically below 10 g/100 ml inclusive of substances which are totally water-insoluble. Examples are medicines, dietary supplements, oral compositions, anti-smoking agents, highly potent sweeteners, pH adjusting agents, flavorings etc.

Other active ingredients are, for instance, paracetamol, benzocaine, cinnarizine, menthol, carvone, caffeine, chlorhexidine-di-acetate, cyclizine hydrochloride, 1,8-cineol, nandrolone, miconazole, mystatine, sodium fluoride, nicotine, cetylpyridinium chloride, other quaternary ammonium compounds, vitamin E, vitamin A, vitamin D, glibenclamide or derivatives thereof, progesterone, acetylsalicylic acid, dimenhydrinate, cyclizine, metronidazole, sodium hydrogen carbonate, the active components from *Ginkgo*, the active components from propolis, the active components from ginseng, methadone, oil of peppermint, salicylamide, hydrocortisone or astemizole.

Examples of active agents in the form of dietary supplements are for instance salts and compounds having the nutritive effect of vitamin B2 (riboflavin), B12, folinic acid, folic acid, niacine, biotine, poorly soluble glycerophosphates, amino acids, the vitamins A, D, E and K, minerals in the form of salts, complexes and compounds containing calcium, phosphorus, magnesium, iron, zinc, copper, iodine, manganese, chromium, selenium, molybdenum, potassium, sodium or cobalt.

Furthermore, reference is made to lists of nutritionists accepted by the authorities in different countries such as for instance US code of Federal Regulations, Title 21, Section 182.5013.182 5997 and 182.8013-182.8997.

Examples of active agents in the form of compounds for the care or treatment of the oral cavity and the teeth are for instance bound hydrogen peroxide and compounds capable of releasing urea during chewing.

Examples of active agents in the form of antiseptics are for instance salts and compounds of guanidine and biguanidine (for instance chlorhexidine diacetate) and the following types of substances with limited water-solubility: quaternary ammonium compounds (for instance ceramine, chloroxylenol, crystal violet, chloramine), aldehydes (for instance paraformaldehyde), compounds of dequaline, polynoxyline, phenols (for instance thymol, para chlorophenol, cresol) hexachlorophene, salicylic anilide compounds, triclosan, halogenes (iodine, iodophores, chloroamine, dichlorocyanuric acid salts), alcohols (3,4 dichlorobenzyl alcohol, benzyl alcohol, phenoxyethanol, phenylethanol), cf. furthermore Martindale, The Extra Pharmacopoeia, 28th edition, pages 547-578; metal salts, complexes and compounds with limited water-solubility, such as aluminum salts, (for instance aluminum potassium sulphate AlK(SO4)2, 12H2O) and furthermore salts, complexes and compounds of boron, barium, strontium, iron, calcium, zinc, (zinc acetate, zinc chloride, zinc gluconate), copper (copper chloride, copper sulfate), lead, silver, magnesium, sodium, potassium, lithium, molybdenum, vanadium should be included; other compositions for the care of mouth and teeth: for instance; salts, complexes and compounds containing fluorine (such as sodium fluoride, sodiummonofluorophosphate, amino fluorides, stannous fluoride), phosphates, carbonates and selenium.

Cf. furthermore J. Dent. Res. Vol. 28 No. 2, pages 160-171, 1949, wherein a wide range of tested compounds is mentioned.

Examples of active agents in the form of agents adjusting the pH in the oral cavity include for instance: acceptable acids, such as adipic acid, succinic acid, fumaric acid, or salts thereof or salts of citric acid, tartaric acid, malic acid, acetic acid, lactic acid, phosphoric acid and glutaric acid and acceptable bases, such as carbonates, hydrogen carbonates, phosphates, sulfates or oxides of sodium, potassium, ammonium, magnesium or calcium, especially magnesium and calcium.

Examples of active agents in the form of anti-smoking agents include for instance: nicotine, tobacco powder or silver salts, for instance silver acetate, silver carbonate and silver nitrate.

In a further embodiment, the sucrose fatty acid esters may also be utilized for increased release of sweeteners including for instance the so-called highly potent sweeteners, such as for instance saccharin, cyclamate, aspartame, thaumatin, dihydrocalcones, stevioside, glycyrrhizin or salts or compounds thereof. For increased released of sweetener, the sucrose fatty acids preferable have a content of palmitate of at least 40% such as at least 50%.

Further examples of active agents are medicines of any type.

Examples of active agents in the form of medicines include caffeine, salicylic acid, salicyl amide and related substances (acetylsalicylic acid, choline salicylate, magnesium salicylate, sodium salicylate), paracetamol, salts of pentazocine (pentazocine hydrochloride and pentazocinelactate), buprenorphine hydrochloride, codeine hydrochloride and codeine phosphate, morphine and morphine salts (hydrochloride, sulfate, tartrate), methadone hydrochloride, ketobemidone and salts of ketobemidone (hydrochloride), beta-blockers, (propranolol), calcium antagonists, verapamil hydrochloride, nifedinpine as well as suitable substances and salts thereof mentioned in Pharm. Int., November 85, pages 267-271, Barney H. Hunter and Robert L. Talbert, nitroglycerine, erythrityl tetranitrate, strychnine and salts thereof, lidocaine, tetracaine hydrochloride, etorphine hydrochloride, atropine, insulin, enzymes (for instance papain, trypsin, amyloglucosidase, glucoseoxidase, streptokinase, streptodornase, dextranase, alpha amylase), polypeptides (oxytocin, gonadorelin, (LH.RH), desmopressin acetate (DDAVP), isoxsuprine hydrochloride, ergotamine compounds, chloroquine (phosphate, sulfate), isosorbide, demoxytocin, heparin.

Other active ingredients include beta-lupeol, Letigen®, Sildenafil citrate and derivatives thereof.

Dental products include Carbamide, CPP Caseine Phospho Peptide; Chlorhexidine, Chlorhexidine di acetate, Chlorhexidine Chloride, Chlorhexidine di gluconate, Hexetedine, Strontium chloride, Potassium Chloride, Sodium bicarbonate, Sodium carbonate, Fluor containing ingredients, Fluorides, Sodium fluoride, Aluminum fluoride.

Ammonium fluoride, Calcium fluoride, Stannous fluoride, Other fluor containing ingredients Ammonium fluorosilicate, Potassium fluorosilicate, Sodium fluorosilicate, Ammonium monofluorphosphate, Calcium monofluorphosphate, Potassium monofluorphosphate, Sodium monofluorphosphate, Octadecentyl Ammonium fluoride, Stearyl Trihydroxyethyl Propylenediamine Dihydrofluoride, Vitamins include A, B1, B2, B6, B12, Folinic acid, Folic acid, niacin, Pantothenic acid, biotine, C, D, E, K. Minerals include Calcium, phosphor, magnesium, iron, Zinc, Cupper, Iod, Mangan, Crom, Selene, Molybden. Other active ingredients include:

Q10®, enzymes. Natural drugs including *Ginkgo biloba*, ginger, and fish oil.

The invention also relates to use of migraine drugs such as Serotonin antagonists: Sumatriptan, Zolmitriptan, Naratriptan, Rizatriptan, Eletriptan; nausea drugs such as Cyclizin, Cinnarizin, Dimenhydramin, Difenhydrinat; hay fever drugs such as Cetrizin, Loratidin, pain relief drugs such as Buprenorfin, Tramadol, oral disease drugs such as Miconazol, Amphotericin B, Triamcinolonaceton; and the drugs Cisaprid, Domperidon, Metoclopramid. In a preferred embodiment the invention relates to the release of Nicotine and its salts.

The following non-limiting examples illustrate different variations of the present invention. The examples are meant for indicating the inventive concept; hence the mentioned examples should not be understood as exhaustive for the present invention.

Figure 1B:
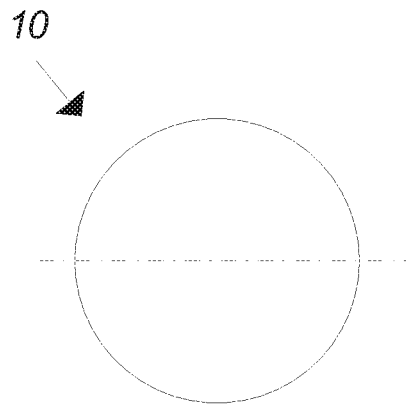

FIGS. 1A and 1B illustrate an embodiment of a chewing gum 10 according to an embodiment of the invention. FIG. 1A shows the chewing gum from the side and FIG. 1B shows the chewing gum from above. In the below description the term tablet or oral tablet refer to a chewing gum.

Figure 4:
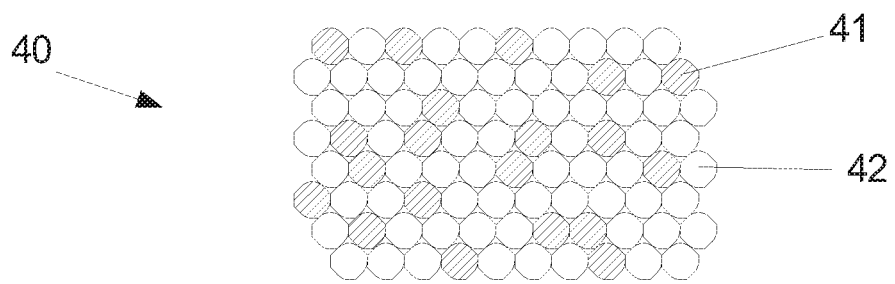
FIGS. 4 and 5 illustrate embodiments of the invention.
Figure 5:
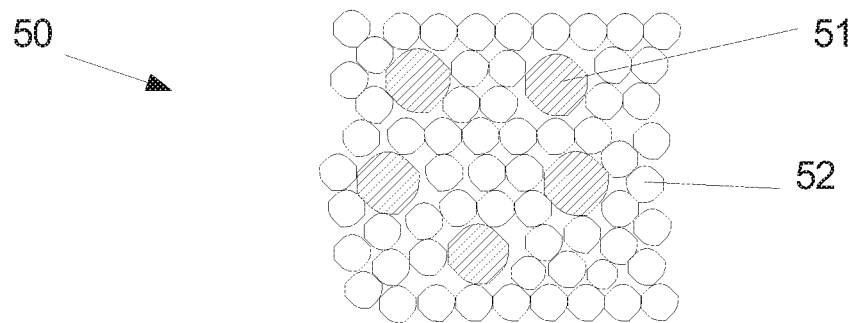

The composition and the way the tablet is or can be made is described elsewhere in the application and details regarding the structure and functioning of this tablet 10 is also indicated and explained further with reference to FIG. 4 and FIG. 5.

Figure 2A:
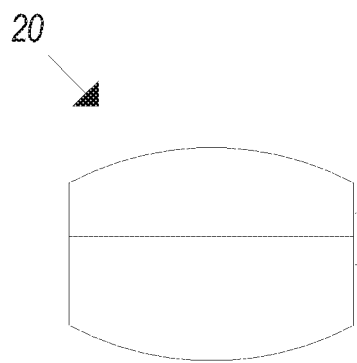
FIGS. 2A and 2B illustrate a two-module version of an embodiment of the invention.
Figure 2B:
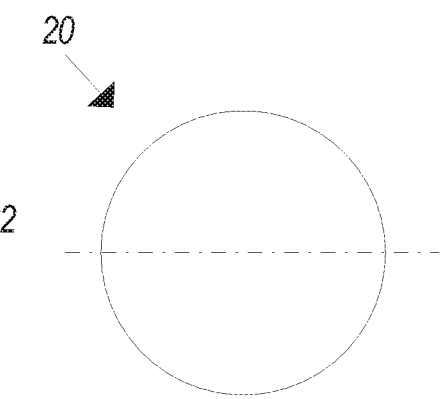

FIGS. 2A and 2B illustrate a two-module version of an oral tablet according to an embodiment of the invention. FIG. 2A shows the oral tablet from the side and FIG. 2B shows the tablet from above.

The composition and the way the tablet is made is described elsewhere in the application.

Figure 6:
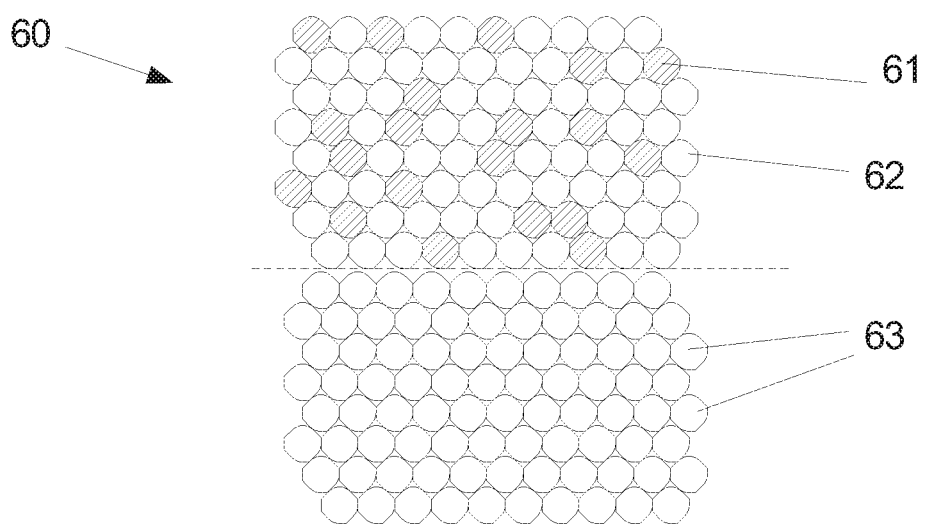
FIG. 6 illustrates a two-module version of an embodiment of the invention.

Details regarding the structure and functioning of this tablet 10 is also indicated and explained further with reference to FIGS. 4, 5 and 6.

The intention with this illustration is to give an example of a physical form, which may be applicable within the scope of the invention. The intention is also to illustrate how the term "a module" is understood and applied throughout the description, i.e. that a module is referring to a population of a plurality particles and the particles have been tableted together to form a module. The term module is applied to indicate that one module comprises one population of tableted particles and another module comprises another population of tableted particles. A population of particles in the present context is thus understood to refer to a plurality of particles. A singular particle is thus of course not understood as a module.

Modules are typically, but not necessarily, distinguishable by the human eye, in particular if the applied compounds in the different modules are formed by differently colored population of particles or mixtures of particles.

The oral tablet 20 comprises an upper module 21 and a lower module 22. The modules, here in the shapes of layers, are thus physically distinct and each comprises a population of particles which has been tableted. The population of the different modules, 21 and 22, may typically be different for many purposes. Examples include use for visual conception, for mechanical purposes e.g. providing strength, for medical purposes, and of course also for maximizing the desired effect of non-DC sugar alcohol contained in the tablet.

In a preferred embodiment, most of the applied non-DC sugar alcohol(s) is comprised in the upper module 21 and the lower module 22 is mostly comprised of DC-components, i.e. components such as sugar alcohols, fillers, flavors, colors etc. conventionally used for direct compression. In embodiments of the invention, a first module, here the lower module 22 may be regarded and applied as a support module supporting another module, here the upper module 21. The benefit of this division in the designing of properties is that the module containing the non-DC sugar alcohol particles may comprises substantial amounts of non-DC sugar alcohol particles even in spite of the fact that the modules own mechanical strength is substantially weakened, as the supporting modules structural strength may be designed to ensure that the overall structural strength of the tablet is sufficient to obtain the desired friability and tablet appearance. This multi-modular design approach is of even more interest as the tablets designed according to this principle benefits, in terms of disintegration and dissolving of the tablet matrix or part thereof during mastication of the tablet, from the increased salivation effect obtained from the applied high content of non-DC sugar alcohol particles in the relatively weak module.

Figure 3A:
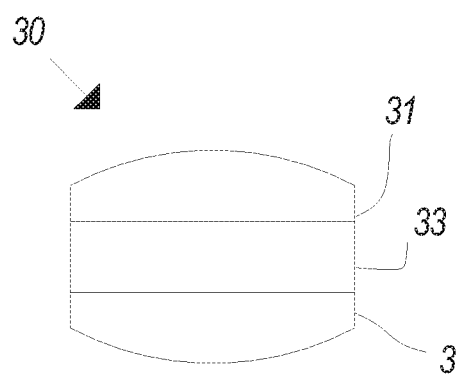
FIGS. 3A and 3B illustrate a three-module version of an embodiment of the invention.
Figure 3B:
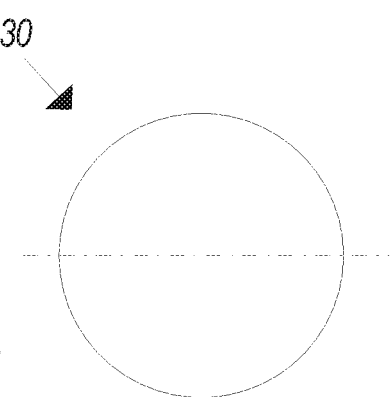

FIGS. 3A and 3B illustrate a three-module version of an oral tablet 30 according to an embodiment of the invention. FIG. 3A shows the oral tablet 30 from the side and FIG. 3B shows the tablet from above.

The illustrated tablet 30 comprises an upper module 31, and intermediate module 33 and a lower module 32.

The upper module 31 may, as explained in relation to the upper module of FIGS. 2A and 2B, be formed by a population of particles comprising an effective amount of non-DC sugar alcohol particles. The intermediate layer may comprise further non-DC sugar alcohol particles and or a desired active ingredient.

The lower module 32 may comprise substantial amounts of DC-particles such as sugar alcohol(s), fillers, some binder and other relevant ingredients enabling the lower module 32 to form a structural support for at least the upper module 31.

FIG. 4 illustrates a part 40 of a cross-section of one of the oral tablets in FIGS. 1-3. The part of the oral tablet, illustrated in FIG. 4 may thus correspond to a view of a part of the upper layers 21 or 31 or a part of the tablet 1.

Such part 40 of a tablet may within the scope of the invention comprise at least two different types of particles, namely non-DC sugar alcohol particles 41 and DC-particles 42. Preferred but non-limiting non-DC sugar alcohols are non-DC erythritol and non-DC xylitol as these non-DC sugar alcohols have shown effective to obtain the desired effect. The illustrated non-DC particles 41, although indicated on the figures with the same graphical expression may of course comprise non-DC sugar alcohol particles of the same type, but also comprise a mixture of two or more non-DC sugar alcohol particles.

The particles are evenly distributed amongst a plurality of DC particles 42 within the specified module. The DC particles 42, although indicated in the figure as same type particles may include different types of DC sugar alcohol particles, flavor particles, binders, etc. The intention with the figure is to illustrate that the non-DC sugar alcohol particles 41 in practice have to be homogenously distributed amongst the DC particles 42 in the final oral tablet 40. It may not be enough that the non-DC particles and DC particles are mixed homogenously at some stage during the preparation of the tableting process. The homogenous mix should preferably be maintained in the final oral tablet 40 in order to promote the desired effect and to obtain a mechanically stable tablet. A further advantageous effect of the evenly distributed non-DC sugar alcohol particles may be obtained through an advantageous and increased salivation during mastication of a tablet.

The understanding and conception of the evenly distribution of the non-DC sugar alcohol particles in the relevant tablet module may in practical terms be very difficult to define as such definitions are very difficult to monitor and control during the processing of the tablet but it has been possible to establish an industrial scale process, where the mixture containing the substantial amounts of non-DC sugar alcohol(s) may be established all the way through the process into the final tablet. Such process may e.g. be validated by test manufacturing of a sequence of tablets where the variation of the non-DC sugar alcohol content of the manufactured tablets are determined.

It is noted that the non-DC particles 41 forms small sub-areas or sub spaces in the final oral tablet or the relevant module of the final tablet, e.g. the upper modules 21 and 31. These sub-areas are elsewhere in the present application referred to as discrete non-DC areas and may be formed by single non-DC particles or very small groups of these non-DC particles. These discrete non-DC areas are thus intended to be contained within a matrix formed by DC-sugar alcohol particles or other DC-particles.

The non-DC areas, in the present embodiment, the non-DC sugar alcohol particles 41 are thus included in substantial amounts in the tablet and from a mechanical perspective supported and contained by the DC-particles 42 and together forming a matrix which, when chewed, may bring the non-DC sugar alcohol particles 41 into contact with the oral cavity and promote salivation. The promoted salivation, together with relatively weak mechanical structure of the module or tablet comprising the non-DC sugar alcohol particles induces a fast breakup of the tablet and thereby pushes the non-DC particles into contact with the oral cavity in a way which is completely different from compressed tablets made from DC-sugar alcohol particles, such as granulated erythritol or xylitol.

The non-DC areas may thus result in induced saliva generation upon mastication of the tablet and also induce and promote a very fast and pleasant dissolving of the tablet matrix or part thereof, when compared to conventional compressed tablets.

Active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this compensation may both compromise salivation effect and texture/mouthfeel during mastication.

FIG. 5 illustrates a part of a cross-section of one of the oral tablets in FIGS. 1-3. The part of the oral tablet, illustrated in FIG. 5 may thus correspond a view of a part of the upper modules 21 or 31 or the tablet 1.

In terms of components applied, the tablet part illustrated in FIG. 5 may largely correspond to the above-described embodiment of FIG. 4, but now the tablet part comprises larger sized non-DC particles 51 containing in a compression of particles of DC particles 52.

The intention with the present FIG. 5 is merely to indicate that in particular the non-DC sugar alcohol particles may be larger in size than the DC particles and it is also noted in this context that the use of larger sized non-DC sugar alcohol particles may indeed increase the obtained salivation or the desired effect.

FIG. 6 illustrates a particular transition in a tablet 60 with two adjacent modules according to an embodiment of the invention. The presently illustrated part of such tablet may e.g. refer to the transition between the modules 21 and 22 of the tablet 20 as seen in FIG. 2A. The tablet 60 comprises non-DC sugar alcohol particles 61 and DC particles 62 in one module and another module comprising DC particles 63. The understanding of a module is here easily conceivable as the population of non-DC sugar alcohol particles 61 and DC particles 62 forms one module and the population of DC particles 63 forms another module. Often, the compositions of the DC sugar alcohol particles 62 and the DC sugar alcohol particles 63 may be different, depending on the specific circumstances.

In the present context, the tablet comprises particles comprising gum base. Thus, when the particles 42, 52 62, 63 above are described as DC sugar alcohol particles, it is merely for illustrative purposes, and could also comprise e.g. a mixture of DC sugar alcohol particles and particles comprising gum base.

Again, in relation to FIG. 5 and FIG. 6, active ingredients may be present as both DC and non-DC particles as long as the active ingredient as such does not interfere significant with other compounds. If the active ingredients are non-DC particles, the amount should be kept low enough to ensure the mechanical stability of the tablet or modules or alternatively compensated by relevant DC-particles or binders. It should be noted that such a compensation should be carefully considered as this may compensation may both compromise salivation effect and texture/mouthfeel during mastication.

Particles comprising gum base, may also be present both as non-DC and DC particles, although DC-particles comprising gum base are highly preferred over non-DC gum base-containing particles. When applying particles comprising gum base, these particles are preferably but not necessarily included in a supporting module as DC particles 63 e.g. with mixed with sugar alcohol particles 63 as illustrated in FIG. 6.

The above illustrated modules are all designed as layers. It is stressed that other shapes of modules may be applicable within the scope of the invention. Non-limiting examples are modules having a sphere shape, diamond shape, oval shape, cone shape, etc. All the relevant shapes must of course be adapted to fit the tableting process according to known measures within the art.

EXAMPLES

Examples 1-7. Gum Bases

Seven different samples, given samples numbers 101-107, of gum bases are provided in Examples 1-7. The compositions are given in table 1 and the samples were prepared by the following process:

Elastomers and about ⅓ of the resin are mixed at 120° C. together with filler in a pre-heated mixer having horizontally placed Z-shaped arms for mixing. The fillers are talc or non-DC calcium carbonate. The mechanical action of the mixer causes shearing and grinding resulting in softening of the elastomers.

When the elastomers are softened, more resin is slowly added to the elastomer, resin and filler until the mixture becomes homogeneous. The remaining resin is then added to the mixer and mixed for 10-20 minutes. The softeners, i.e. emulsifier, wax and vegetable fat, are then added and mixed for 20-40 minutes until the whole mixture becomes homogeneous.

After a total mixing time of about 45-60 minutes, the mixture is subjected to pelletizing in a standard under water pelletizing (UWP) unit resulting in coherent granules with an average diameter of approximately 1 mm.

The applied polyisobutylene may eg. be Oppanol B12, polyvinyl acetate (PVA) may eg. be Vinnapas B 1.5 sp, VA-VL copolymers (vinyl acetate—vinyl laurate copolymers) may eg. be Vinnapas B 500/20 VL, natural resin may eg. be Staybelite 5E or Piccolyte C85, softener may eg. be hydrogenated vegetable fat such as hydrogenated sunflower oil, Bulk sweetener may eg. be sorbitol, flavor may eg. be menthol crystals. It is stressed that the specifically mentioned components are of course a non-limiting disclosure intended to assist a skilled person in reproducing the present invention.

In case of Example 7 (sample no. 107), the homogeneous mixture is not subjected to pelletizing but merely discharged into a pan and allowed to cool to room temperature.

Then the mixture is added to another mixer having horizontally placed Z-shaped arms for mixing operating at a temperature of about 40° C. Bulk sweetener is added and mixed until a homogenous mass is obtained.

The mass is discharged and cooled by liquid nitrogen before being introduced to a milling device, in which the mass is milled to obtain particulate material that is ready for tableting.

TABLE 1

Numbers are given in percent by weight of the gum base

| Gum base | Ex. 1 | Ex. 2 | Ex. 3 | Ex. 4 | Ex. 5 | Ex. 6 | Ex. 7 |
|---|---|---|---|---|---|---|---|
| Sample no. | 101 | 102 | 103 | 104 | 105 | 106 | 107 |
| Elastomers (butyl rubber and polyisobutylene) | 18 | 21 | 21 | 10 | 10 | 5 | 16 |
| Resins (polyvinyl acetate (PVA), VA-VL copolymers and natural resins (ester gums and terpene resins) | 38 | 44 | 44 | 50 | 50 | 55 | 31 |
| Softeners (wax, fats, emulsifiers) | 23 | 21 | 21 | 22 | 23 | 20 | 19 |
| Filler (talc) | 18 | 11 | | | 17 | 20 | 14 |
| Filler (Calcium carbonate) | | | 12 | 15 | | | |
| Bulk sweetener | | | | | | | 20 |
| Flavor | 3 | 3 | 2 | 3 | | | |
| Total | 100 | 100 | 100 | 100 | 100 | 100 | 100 |

Example 8-22

Preparation of Tablets

Tablets according to Examples 8-22 using the compounds as outlined below in Table 2, Table 3 and Table 4 were prepared as follows:

The compounds of Examples 1-7 are present in the form of particles/granules.

The particulate compounds of Examples 1-7 and further tablet compounds are weighed into the proper amounts according to the exampled compositions of Table 2 to Table 4.

The weighed amounts are then added to a Turbula mixer in a stainless steel container and blended at 50 rpm for 4 minutes and then adding magnesium stearate and blending one additional minute.

The mixtures are then tableted by means of a Piccola RIVA DC-SC-041-2. A Fette 3090i may also be used.

The resulting tablets according to Examples 8-22 are then obtained by tableting with a suitable pressure force.

For each tablet of examples 8-22, the second layer as outlined in Table 2, Table 3 and Table 4 is pressed initially at a first relatively low pressure. The blended composition of the so-called first layer, i.e. compositions of Table 2 to 4 is then fed to the mold and a final two-layer tablet is then compressed at higher pressure than the pressure applied on the first layers, thereby producing final two-layer tablets according to Examples 8-17. It is noted that the final two-layer tablets of the present examples are 2.0 gram tablets and that the first layer of the tablets weighs 0.9 gram and the second layer of the tablets weighs 1.1 gram.

TABLE 2

Numbers are given in percent by weight of each layer of the tablet

| | Ex 8 | Ex 9 | Ex 10 | Ex 11 | Ex 12 |
|---|---|---|---|---|---|
| Raw material (wt %) First layer | | | | | |
| Non-DC Erythritol | 48 | 48 | 50 | 50 | 48 |
| DC Isomalt | 47.75 | 45.75 | 43.75 | 41.75 | |
| Sorbitol | — | — | — | — | 48.75 |
| Flavor | 2 | 2 | 4 | 4 | 2 |
| High Intensity Sweetener (HIS) | 0.25 | 0.25 | 0.25 | 0.25 | 0.25 |
| Magnesium Stearate | 1 | 1 | 1 | 1 | 1 |
| Binder HPC | 1 | 3 | 1 | 3 | — |
| Raw material (wt %) Second layer | | | | | |
| Gum base sample no. 101 | 30 | 20 | 10 | 40 | 30 |
| Gum base sample no. 102 | 10 | 20 | 30 | 0 | 10 |
| DC Xylitol | 27.50 | 27.75 | — | — | 54.50 |
| Non-DC Xylitol | 27 | 27 | — | — | — |
| DC Isomalt | — | — | 27.50 | 27.75 | — |
| Non DC Isomalt | — | — | 27 | 27 | — |
| Salivation flavor | 0.25 | — | 0.25 | — | 0.25 |
| Flavor | 4 | 4 | 4 | 4 | 4 |
| HIS | 0.25 | 0.25 | 0.25 | 0.25 | 0.25 |
| Magnesium Stearate | 1 | 1 | 1 | 1 | 1 |
| Friability % | 2.9 | 1.7 | 2.76 | 1.58 | 0.77 |

TABLE 3

Examples with different types of active ingredients. Numbers are given in percent by weight of each layer of the tablet

| | Ex 13 | Ex 14 | Ex 15 | Ex 16 | Ex 17 |
|---|---|---|---|---|---|
| Raw material (wt %) First layer | | | | | |
| Non-DC Erythritol | 48 | 48 | 48 | 48 | 48 |
| DC Isomalt | 47.75 | 47.75 | 27.75 | 47.75 | 47.75 |
| Flavor | 2 | 2 | 2 | 2 | 2 |
| HIS | 0.25 | 0.25 | 0.25 | 0.25 | 0.25 |
| Magnesium Stearate | 1 | 1 | 1 | 1 | 1 |
| Binder HPC | 1 | 1 | 1 | 1 | 1 |
| CaCO3 (antacid) | | | 20 | | |

TABLE 3-continued

Examples with different types of active ingredients. Numbers are given in percent by weight of each layer of the tablet

|  | Ex 13 | Ex 14 | Ex 15 | Ex 16 | Ex 17 |
|---|---|---|---|---|---|
| Raw material (wt %) Second layer | | | | | |
| Gum base sample no. 101 | 20 | 20 | 20 | 20 | 20 |
| Gum base sample no. 102 | 20 | 20 | 20 | 20 | 20 |
| DC Xylitol | 27.55 | 22.75 | 27.75 | 26.75 | 27.25 |
| Non-DC Xylitol | 27 | 27 | 27 | 27 | 27 |
| Flavor | 4 | 4 | 4 | 4 | 4 |
| HIS | 0.25 | 0.25 | 0.25 | 0.25 | 0.25 |
| Magnesium Stearate | 1 | 1 | 1 | 1 | 1 |
| Nicotine | 0.2 | | | | |
| Caffeine | | 5 | | | |
| Bromhexine | | | | 1 | |
| Diphenhydramine | | | | | 0.5 |

TABLE 4

Examples with different oral care or nutraceutical embodiments. Numbers are given in percent by weight of each layer of the tablet

|  | Ex 18 | Ex 19 | Ex 20 | Ex 21 | Ex 22 |
|---|---|---|---|---|---|
| Raw material (wt %) First layer | | | | | |
| Non-DC Erythritol | 48 | 48 | 48 | 48 | 48 |
| DC Isomalt | 47.75 | 47.75 | 47.75 | 47.75 | 47.75 |
| Flavor | 2 | 2 | 2 | 2 | 2 |
| HIS | 0.25 | 0.25 | 0.25 | 0.25 | 0.25 |
| Magnesium Stearate | 1 | 1 | 1 | 1 | 1 |
| Binder HPC | 1 | 1 | 1 | 1 | 1 |
| Raw material (wt %) Second layer | | | | | |
| Gum base sample no. 101 | 20 | 20 | 20 | 20 | 20 |
| Gum base sample no. 102 | 20 | 20 | 20 | 20 | 20 |
| DC Xylitol | 27.295 | 27.025 | 22.188 | 25.03 | 24.55 |
| Non-DC Xylitol | 27 | 27 | 27 | 27 | 27 |
| Flavor | 4 | 4 | 4 | 4 | 4 |
| Magnesium Stearate | 1 | 1 | 1 | 1 | 1 |
| HIS | 0.25 | 0.25 | 0.25 | 0.25 | 0.25 |
| Sodium fluoride | 0.022 | 0.022 | 0.022 | 0.02 | 0.023 |
| Zinc acetate | 0.433 | 0.433 | 0.430 | — | — |
| Sodium bicarbonate | — | 0.270 | 0.270 | — | — |
| Calcium pyrophosphate | — | — | 4.84 | 2.7 | 2.702 |
| Vitamin D3 premix | — | — | — | — | 0.475 |

A specification of relevant compounds applied in the examples explained above are listed below.

HPC: Hydroxy propyl cellulose. Klucel Nutra D from Ashland
Non DC Xylitol: Xivia C from Dupont
Non granulated Sorbitol: Pharm Sorbidex P 16656 from Cargill
Non DC Isomalt: Isomalt GS from Beneo Paltinit
Non DC Mannitol: Pearlitol from Roquette
Non DC Maltitol: Maltisorb. P200 from Roquette
Non DC Erythritol: Zerose 16952 from Cargill
DC Erythritol—Zerose 16966 from Cargill
DC Xylitol—Xylitab 200 from Dupont
DC Isomalt—Isomalt DC 101 from Beneo Paltinit
DC Mannitol—Pearlitol SD200 from Roquette
DC Maltitol—Sweetpearl 300 DC from Roquette

TABLE 5

Sensory evaluation of examples 8-12.

| Ex | Total sensory experience Good/ Acceptable(Acc)/Poor | Suitable mouthfeel during 10 minutes of chewing | Initial Watering effect 1-5 1 low 5 high |
|---|---|---|---|
| 8 | Acc. | Nice crunchy initial chew. Fast dissolving mint layer. Nice cooling mouthfeel and flavor burst. Ok softness texture. Ok lasting watering effect | 5 |
| 9 | Good | Nice crunchy initial chew. Fast dissolving mint layer. Nice cooling mouthfeel and flavor burst. Soft texture. Long lasting watering effect | 4 |
| 10 | Acc | Nice crunchy fast dissolving mint layer. High flavor burst. Sandy particles over a long chewing period. Soft texture Long lasting watering effect | 5 |
| 11 | Poor | Nice crunchy fast dissolving mint layer. Lower flavor burst. Sandy particles over a long chewing period. A bit hard texture over time Some lasting watering effect | 3 |
| 12 | Good | Soft crunchy initial chew. Fast dissolving mint layer Fast flavor burst and high juiciness. Long lasting watering effect | 4 |

Evaluation

The tablets of Example 8-12 were evaluated with respect to mouthfeel.

The friability of Examples 8-12 was also measured according to European Pharmacopoeia 9.1, test method 2.9.7. by using a pharmaceutical friability-tester PTF 10E from Pharma Test.

The tablets of Example 8-12 were evaluated with respect to mouthfeel.

The tablets were evaluated with respect to the elastomer content versus tablet performance. It was noted that when using Examples 1 and 2, with a relatively high amount of elastomer increased the textural perception, the initial chew, but it was also noted that an increased salivation was still obtained when compared to embodiments based on DC-erythritol in the first layer instead of the non-DC erythritol applied in Examples 8-12. The increased amount of elastomer thus not only improved the mouthfeel and initial chew, but is also does so without losing significant salivation effect.

In particular Examples 8 and 12 were mentioned as having a very attractive and nice initial crunch and the tablet polyols was dissolving very fast when masticated. It is noted in this context that the perceived salivation also promoted an initial fast transition of the particles comprising gum base into a coherent residual.

It was also noted that the flavor perception was more fresh even in spite of the fact the applied flavor and amount of flavor was the same in both the inventive Examples and the "conventional" comparative examples (not shown) based on DC-erythritol in the first layer instead of the non-DC erythritol applied in Examples 8-12.

In terms of active ingredients, Examples 13-17 did exhibit an attractive mouthfeel, an attractive taste and the tablet was unexpectedly considered attractive in terms of e.g. buccal delivery of active ingredients, such as nicotine of example 13. Also active ingredients such as the caffeine Example 14 were considered surprisingly pleasant when considering that caffeine is known for its bitter taste.

Overall, the salivation was considered impressive.

It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A tableted chewing gum suitable for active pharmaceutical ingredients, the tableted chewing gum comprising a population of particles and having been formed by direct compression, the population of particles comprising a) directly compressible (DC) sugar alcohol particles, b) non-directly compressible (non-DC) sugar alcohol particles and c) DC particles comprising gum base, the gum base comprising at least 5% by weight of elastomer, wherein the non-DC sugar alcohol particles provide the tableted chewing gum with a plurality of discrete non-DC areas embedded in a matrix comprising the DC sugar alcohol particles, that result in induced saliva generation upon mastication of the tableted chewing gum, wherein the non-DC sugar alcohol particles have not been granulated prior to tableting, and wherein the non-DC sugar alcohol particles have the average size at least 50 µm larger than the average size of the DC sugar alcohol particles.

2. The tableted chewing gum according to claim 1, wherein said population of particles, including a), b) and c), is comprised in a first tableted module of the tableted chewing gum and combined with a second population of particles that is comprised in a second tableted module of the tableted chewing gum.

3. The tableted chewing gum according to claim 1, wherein a) and b) is comprised in a first tableted module of the tableted chewing gum and c) is comprised in a second tableted module of the tableted chewing gum, wherein the first tableted module of the tableted chewing gum is free of gum base.

4. The tableted chewing gum according to claim 1, wherein the tableted chewing gum comprises at least 20% by weight of gum base.

5. The tableted chewing gum according to claim 1, wherein the non-DC sugar alcohol particles are selected from the group consisting of non-DC particles of erythritol, non-DC particles of maltitol, non-DC particles of xylitol, and combinations thereof.

6. The tableted chewing gum according to claim 1, wherein the non-DC sugar alcohol particles are non-DC erythritol particles.

7. The tableted chewing gum according to claim 1, wherein the tableted chewing gum comprises said non-DC sugar alcohol particles in an amount of at least 10% by weight of the tableted chewing gum.

8. The tableted chewing gum according to claim 1, wherein saliva generation upon the mastication of the tableted chewing gum is induced compared to a tableted chewing gum where the discrete non-DC areas are based on DC sugar alcohol particles.

9. The tableted chewing gum according to claim 1, wherein the tableted chewing gum generates more than 1.0 mL saliva per 10 seconds within 30 seconds from onset of mastication.

10. The tableted chewing gum according to claim 1, wherein the tableted chewing gum generates more than 0.5 mL saliva per 10 seconds within a period from 30 to 90 seconds from onset of mastication.

11. The tableted chewing gum according to claim 1, wherein the tableted chewing gum further comprises an active pharmaceutical ingredient.

12. The tableted chewing gum according to claim 1, wherein the tableted chewing gum further comprises an oral care agent in an amount of at least 0.1% by weight of the tableted chewing gum.

13. The tableted chewing gum according to claim 1, wherein the tableted chewing gum further comprises dentifrice in an amount of at least 0.1% by weight of the tableted chewing gum.

14. The tableted chewing gum according to claim 1, wherein the tableted chewing gum does not comprise an orally disintegrating tablet (ODT) module.

15. A tableted chewing gum suitable for active pharmaceutical ingredients, the tableted chewing gum comprising a population of particles and having been formed by direct compression, the population of particles comprising a) directly compressible (DC) sugar alcohol particles, b) non-directly compressible (non-DC) sugar alcohol particles and c) DC particles comprising gum base, the gum base comprising at least 5% by weight of elastomer, wherein the non-DC sugar alcohol particles provide the tableted chewing gum with a plurality of discrete non-DC areas embedded in a matrix comprising the DC sugar alcohol particles, wherein the non-DC sugar alcohol particles have not been granulated prior to tableting, and wherein the non-DC sugar alcohol particles have the average size at least 50 µm larger than the average size of the DC sugar alcohol particles.

16. The tableted chewing gum according to claim 15, wherein the tableted chewing gum has a weight ratio between said non-DC sugar alcohol particles and said DC sugar alcohol particles that is between 0.3 and 1.2.

17. A tableted chewing gum suitable for active pharmaceutical ingredients, the tableted chewing gum comprising a population of particles and having been formed by direct compression, the population of particles comprising a) directly compressible (DC) sugar alcohol particles, b) non-directly compressible (non-DC) sugar alcohol particles and c) DC particles comprising gum base, the gum base comprising at least 5% by weight of elastomer, wherein the tableted chewing gum does not comprise nicotine, wherein the non-DC sugar alcohol particles provide the tableted chewing gum with a plurality of discrete non-DC areas embedded in a matrix comprising the DC sugar alcohol particles, wherein the non-DC sugar alcohol particles have not been granulated prior to tableting, and wherein the non-DC sugar alcohol particles have the average size at least 50 µm larger than the average size of the DC sugar alcohol particles.

18. The tableted chewing gum according to claim 17, wherein said population of particles, including a), b) and c), is comprised in a first tableted module of the tableted chewing gum and combined with a second population of particles that is comprised in a second tableted module of the tableted chewing gum.

19. The tableted chewing gum according to claim 17, wherein a) and b) is comprised in a first tableted module of the tableted chewing gum and c) is comprised in a second tableted module of the tableted chewing gum, wherein the first tableted module of the tableted chewing gum is free of gum base.

20. The tableted chewing gum according to claim 17, wherein the tableted chewing gum comprises said non-DC sugar alcohol particles in an amount of at least 10% by weight of the tableted chewing gum.

* * * * *